United States Patent
Ahani

(10) Patent No.: US 11,205,157 B2
(45) Date of Patent: Dec. 21, 2021

(54) TECHNIQUES FOR COMMUNICATING DYNAMICALLY IN A MANAGED SERVICES SETTING

(71) Applicant: Project Revamp, Inc., Hillsborough, CA (US)

(72) Inventor: Hessam Ahani, Hillsborough, CA (US)

(73) Assignee: Project Revamp, Inc., Hillsborough, CA (US)

( * ) Notice: Subject to any disclaimer, the term of this patent is extended or adjusted under 35 U.S.C. 154(b) by 168 days.

(21) Appl. No.: 16/240,633

(22) Filed: Jan. 4, 2019

(65) Prior Publication Data

US 2020/0219065 A1 Jul. 9, 2020

(51) Int. Cl.
*G06Q 10/10* (2012.01)
*G16H 40/20* (2018.01)
*G16H 10/60* (2018.01)
*G06F 16/23* (2019.01)

(52) U.S. Cl.
CPC ..... *G06Q 10/1095* (2013.01); *G06F 16/2379* (2019.01); *G16H 10/60* (2018.01); *G16H 40/20* (2018.01)

(58) Field of Classification Search
None
See application file for complete search history.

(56) References Cited

U.S. PATENT DOCUMENTS

| 8,898,798 B2* | 11/2014 | Rogers | G16H 10/60 726/26 |
| 2011/0153380 A1* | 6/2011 | Velusamy | G06Q 10/1095 705/7.19 |
| 2012/0035925 A1* | 2/2012 | Friend | G06F 3/167 704/235 |

(Continued)

FOREIGN PATENT DOCUMENTS

| EP | 2876590 A1 * | 5/2015 | ......... G06Q 10/1095 |
| WO | WO-2016134307 A1 * | 8/2016 | ............ G06Q 10/10 |

OTHER PUBLICATIONS

Praveena, MD Anto, J. Sai Krupa, and S. SaiPreethi. "Statistical Analysis of Medical Appointments Using Decision Tree." 2019 Fifth International Conference on Science Technology Engineering and Mathematics (ICONSTEM). vol. 1. IEEE, 2019. (Year: 2019).*

(Continued)

*Primary Examiner* — Matthew S Gart
*Assistant Examiner* — Derick J Holzmacher
(74) *Attorney, Agent, or Firm* — Perkins Coie LLP

(57) ABSTRACT

Methods to update a database and forward a communication are disclosed. A method to update a database may include a service provider device receiving a first communication in one of a plurality of communication formats, the first communication including unknown content that is interpretable by the service provider device. The service provider device may parse the first communication to discover a request to modify a schedule of a plurality of events stored in the service provider database. The service provider device (Continued)

may modify the schedule in accordance with the request. The service provider device may send a second communication indicating that the schedule has been modified in accordance with the request or seeking information required to complete the modification.

20 Claims, 15 Drawing Sheets

(56) References Cited

U.S. PATENT DOCUMENTS

| | | | |
|---|---|---|---|
| 2014/0136259 A1* | 5/2014 | Kinsey, II | G06Q 10/063116 705/7.16 |
| 2015/0347705 A1* | 12/2015 | Simon | G16H 50/30 705/3 |
| 2016/0048780 A1* | 2/2016 | Sethumadhavan | G06Q 10/0633 705/2 |
| 2017/0124526 A1* | 5/2017 | Sanderford | G06Q 10/1095 |
| 2017/0344704 A1* | 11/2017 | Ch | G16H 20/00 |
| 2017/0344948 A1* | 11/2017 | Kumar | G16H 10/60 |
| 2017/0359334 A1* | 12/2017 | Maddox | G10L 17/06 |
| 2017/0364600 A1* | 12/2017 | Sadauskas, Jr. | G06F 16/248 |
| 2018/0144308 A1* | 5/2018 | Lips | G06Q 10/1095 |
| 2018/0294048 A1* | 10/2018 | Blumenthal | G06Q 10/1095 |
| 2018/0315428 A1* | 11/2018 | Johnson | G10L 15/01 |
| 2018/0374475 A1* | 12/2018 | Lewis | G06N 20/10 |
| 2019/0115104 A1* | 4/2019 | Uske | G06F 3/167 |
| 2019/0237203 A1* | 8/2019 | Schwabl | G06Q 10/1095 |
| 2020/0126550 A1* | 4/2020 | Kim | G16H 10/60 |
| 2020/0371744 A1* | 11/2020 | Liao | H04M 11/10 |
| 2021/0082317 A1* | 3/2021 | Hoppmann | G16H 10/60 |
| 2021/0174800 A1* | 6/2021 | Srinivasan | G06F 3/167 |
| 2021/0225495 A1* | 7/2021 | Rusak | G16H 40/20 |

OTHER PUBLICATIONS

Anitha, K., et al. "Virtual Medical Assistant Using Machine Learning." International Journal of Research in Engineering, Science and Management 4.6 (2021): 209-215. (Year: 2021).*

Sadman, Nafiz, et al. "Recommend Speciality Doctor from Health Transcription: Ensemble Machine Learning Approach." 2021 IEEE 11th Annual Computing and Communication Workshop and Conference (CCWC). IEEE, 2021. (Year: 2021).*

* cited by examiner

500

```
┌─────────────────────────────────────────────────────────────┐
│ Receive a first communication in one of a plurality of      │
│ communication formats, the first communication including    │──502
│ unknown content that is interpretable by the service        │
│ provider device                                             │
└─────────────────────────────────────────────────────────────┘
                              │
┌─────────────────────────────────────────────────────────────┐
│ Parse the first communication to discover a request from a  │
│ first client to modify a schedule of a plurality of events  │──504
│ stored in the service provider database                     │
└─────────────────────────────────────────────────────────────┘
                              │
┌─────────────────────────────────────────────────────────────┐
│ Modify the schedule in accordance with the request based on │
│ a rule of a plurality of rules that matches the request     │──506
└─────────────────────────────────────────────────────────────┘
                              │
┌─────────────────────────────────────────────────────────────┐
│ Send a second communication in one of the plurality of      │
│ communication formats selected based on association with    │──508
│ the client in the service provider database                 │
└─────────────────────────────────────────────────────────────┘
```

FIGURE 5

TECHNIQUES FOR COMMUNICATING DYNAMICALLY IN A MANAGED SERVICES SETTING

TECHNICAL FIELD

Various embodiments concern communication between multiple devices, and more particularly, concern receiving information from devices and updating a database based on communicated information.

BACKGROUND

Managed service providers offer a variety of services to clients. For example, in a dental practice, dentists and support staff work to perform dental procedures for clients. Many service providers may have multiple scheduled appointments to perform services for clients. To record the scheduled appointments, many service providers maintain an electronic calendar. The electronic calendar may include information representing multiple appointments, where each appointment includes at least client information, the services to be provided, and an appointment time.

Clients may interact with service providers via various communication channels, such as in person or over the phone, for example. In many environments, a client creates an appointment with the service provider by interacting with the service provider and communicating the nature of the services to be provided in the appointment. The service provider may determine an available time for the new appointment and notify the client of the available time(s). When the appointment is created, the service provider may update the electronic calendar to include the new appointment.

The service provider may later notify the client as to an upcoming appointment. The notification may be transmitted via a suitable communication method (e.g. phone, text, email, standard mail service, etc.). The service provider may maintain records of the electronic calendar and client information digitally using a computing device.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 5 illustrates a flow diagram illustrating a method to maintain a service provider database, consistent with various embodiments.

Figure 1:
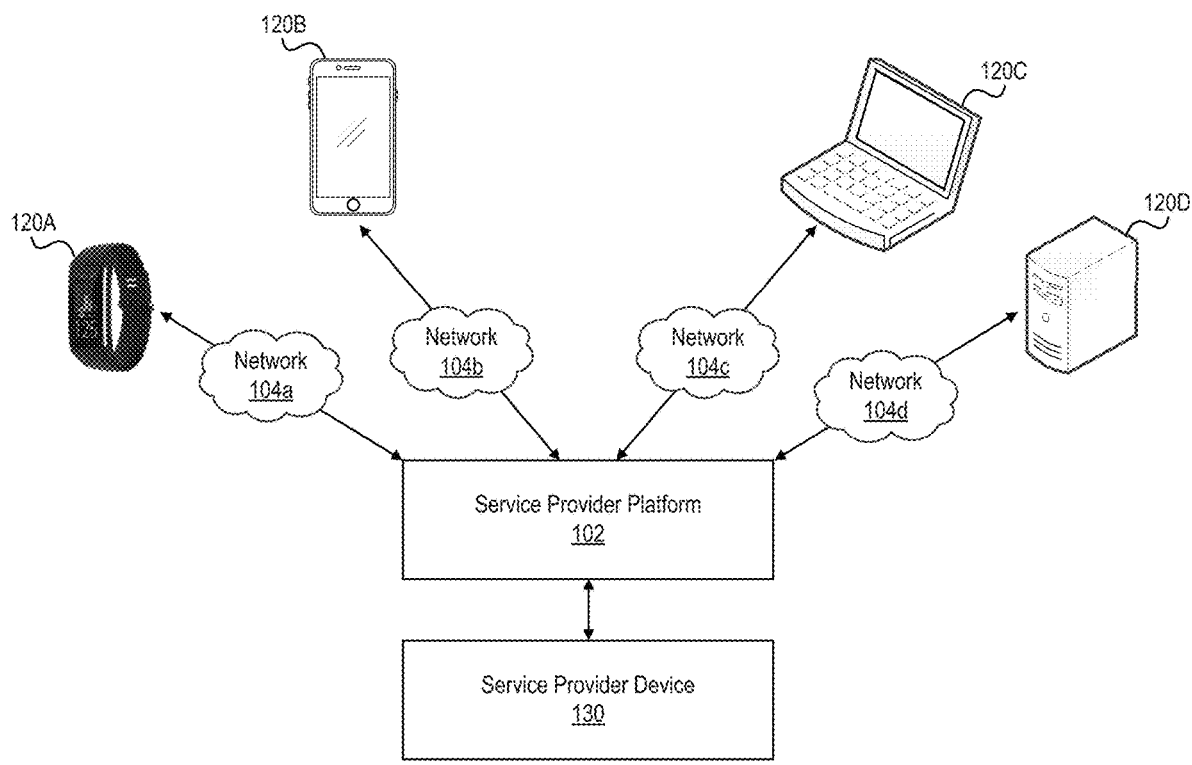
FIG. 1 illustrates a communication environment including a service provider platform configured to communicate with several different computing devices.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Embodiments may be described with reference to particular computer programs, system configurations, networks, etc. However, those skilled in the art will recognize that these features are equally applicable to other computer program types, system configurations, network types, etc. For example, although the term "Wi-Fi network" may be used to describe a network, the relevant embodiment could be deployed in another type of network.

Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device (e.g., a base station or a network-connected computer server) to examine video content generated by an electronic device, identify elements included in the video content, apply a classification model to determine an appropriate action, and perform the appropriate action.

Overview

Managed service providers perform a variety of services to clients. For example, the managed service provider may include a dental practice performing various dental procedures for clients. Such service providers may have multiple appointments scheduled for various clients. In response, service providers may maintain a calendar for an upcoming calendar period to track the upcoming scheduled appointments. The calendar may be maintained digitally on a computing device, which may be referred to as an electronic calendar. In some embodiments, the electronic calendar may comprise a database maintained by a computing device, (e.g., computer or server).

A scheduled appointment in the electronic calendar may include information such as client information, the appointment time, the procedure to be performed, an estimated time to perform the procedure, etc. This information may be utilized by the service provider to prepare for each scheduled appointment. The electronic calendar may include a separate appointment calendar for each service provider employee, such as for every dentist in a dental practice, for example.

Generally, to schedule an upcoming appointment, a client interacts with a service provider using a communication channel such as via phone, email, in person, etc. During this interaction, the client may schedule or modify an appointment, and provide other relevant information to the service provider. In response to this interaction, the service provider may update the appointment calendar to include the new or modified appointment and update their information records to include the relevant information provided by the client.

Further, service providers may maintain records that include information relating to clients. Such records may be maintained electronically, such as on a computer-maintained database, for example. Relevant records pertaining to clients may include medical records, personal information records, records indicating past services performed, etc.

Service providers may generally attempt to maintain an appointment calendar that is fully occupied with upcoming client appointments, as each fulfilled appointment may increase utilization and efficiency for the service provider. Additionally, unfilled appointment times in an appointment calendar may lower efficiency and utilization for a service provider.

In many service provider settings, communications from multiple clients may be received in succession. For example, clients may contact the service provider via various communication channels, such as via text message, phone, or email. Service providers may determine the identity of the client associated with each communication, determine the nature of the communication, and update service provider appointment calendars and/or records accordingly.

However, when a plurality of communications are received by a service provider, a portion of the communications may not be properly addressed. Generally, the nature of such communications may be unknown to the service provider at the time of receipt. For example, a service provider may receive multiple communications via both audio (phone) and text (email) format. For purposes of illustration, in this example, due to the lack of uniformity in the communication channels of the requests, the service provider may respond to and update records with respect to the text-based communications but not properly respond to the audio-based communications. Additionally, some communications may be received by the service provider, but not properly addressed due to the large number of communications received and/or improper analysis of the communication.

In some embodiments, when a plurality of communications are received by a service provider via various communication channels, some communications may be improperly interpreted by the service provider. For example, audio communications may be improperly recorded due to an inability to discern the client and/or nature of the communication via audio. Improperly recorded appointments or records may fail to properly update the database based on the communication. Such failures may cause unfilled or double-booked appointments which may lead to decreased efficiency of the service provider.

Client Communication System Overview

FIG. 1 illustrates a communication environment 100 including a service provider platform 102 configured to communicate with several different electronic devices. Here, for example, the service provider platform 102 may communicate with multiple electronic devices, including a wearable smart device 120A, mobile phone 120B, laptop computer 120C, and network-accessible server system 120D (collectively referred to as "electronic devices"). Each electronic device may be associated with an individual, such as a client or employee of a service provider. The association between the electronic device and an individual may include identification information that may allow for the identification of the device and/or the individual associated with the device.

The electronic devices 120A-D may be connected to the service provider platform 102 via one or more networks 104a-d. The network(s) 104a-d can include PANs, LANs, WANs, MANs, cellular networks, the Internet, etc. Additionally or alternatively, the electronic devices 120A-D may communicate with one another over a communication protocol such as Wi-Fi, Bluetooth®, Near Field Communication (NFC), etc.

As shown in FIG. 1, electronic devices 120A-D may communicate with the service provider platform 102. In some embodiments, the service provider platform 102 may execute on the service provider device 130 (e.g., in the form of a computer application). The service provider device 130 executing the service provider platform 102 may include a computing device or series of interconnected computing devices.

In some embodiments, the service provider platform 102 may receive communications from electronic devices (e.g., mobile phone 120B, laptop computer 120C, etc.) concurrently or in succession. In response, the service provider platform 102 may identify the individual and/or electronic device, determine the nature of each communication, and update one or more databases based on each communication. These steps will be described in greater detail below.

Figure 2:
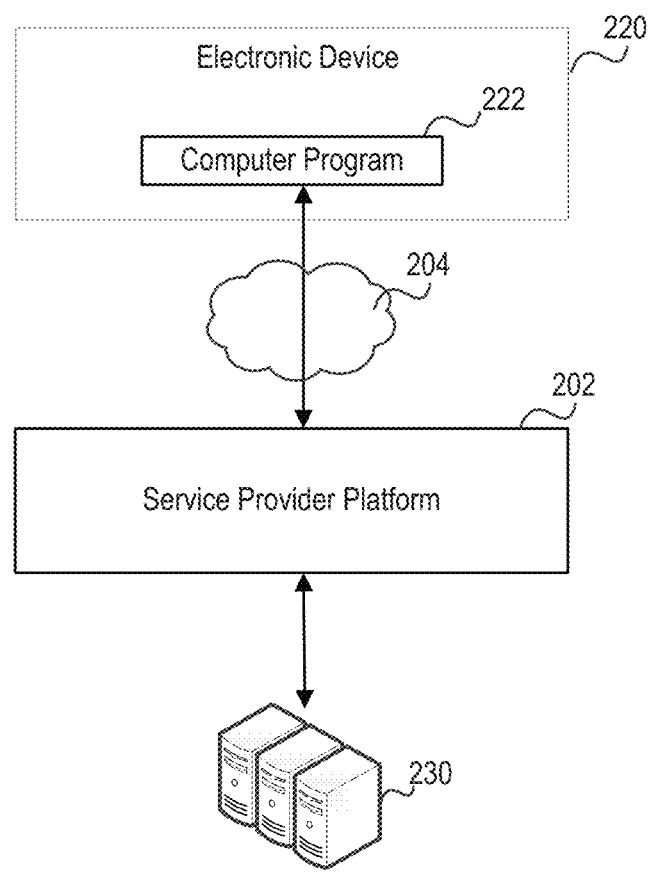
FIG. 2 illustrates a network environment, consistent with various embodiments.

FIG. 2 illustrates a network environment 200, consistent with various embodiments. As shown in FIG. 2, the service provider platform 202 may execute on a service provider device 230. The service provider device 230 may include a computing device, such as a computer, server, or series of servers interconnected via a network. Information and data may be stored and transmitted between the interconnected computing devices of the service provider device 230. In some embodiments, the service provider platform 202 may be executed by a cloud computing service operated by Amazon Web Services® (AWS), Google Cloud Platform™, Microsoft Azure®, or a similar technology.

An electronic device 220 may include instructions to execute a computer program 222. A computer program 222 executing on an electronic device 220 may communicate with the service provider platform 202 via network 204. The network 204 can include personal area networks (PANs), local area networks (LANs), wide area networks (WANs), metropolitan area networks (MANs), cellular networks, the Internet, etc.

The computer program 222 may be accessible via a web browser, desktop application, mobile application, or over-the-top (OTT) application. Accordingly, the computer program 222 may be viewed on an electronic device 220, such as a personal computer, tablet computer, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or another electronic device.

In some embodiments, the service provider platform 202 may generate a client profile to identify a client, such as a client, patient, or employee of a service provider. Electronic device 220 may transmit client profile information, such as a client name, contact information, username and password, credentials, etc., to the service provider platform 202. In response, the service provider platform 202 may generate a client profile associating a client to identification information provided. The service provider platform 202 may access a listing of individual information and associated client profile information to identify an individual and an associated client profile. The client profile information may be stored at the service provider device 230.

In some embodiments, the client profile may include device identification information to identify an electronic device associated with the client. Such device identification information may include, for example, a device serial number, MAC address, internet protocol (IP) address, or a license key.

Service provider platform 202 may access a plurality of client profiles and associated identification information, where each client profile may be unique to a client. In some embodiments, the service provider platform 202 may include a client profile registry that includes the client profiles and associated identification information and/or device identification information to identify a client and/or client device. Client profiles and associated client profile information and/or device identification information may be stored at the service provider device 230.

Figure 3:
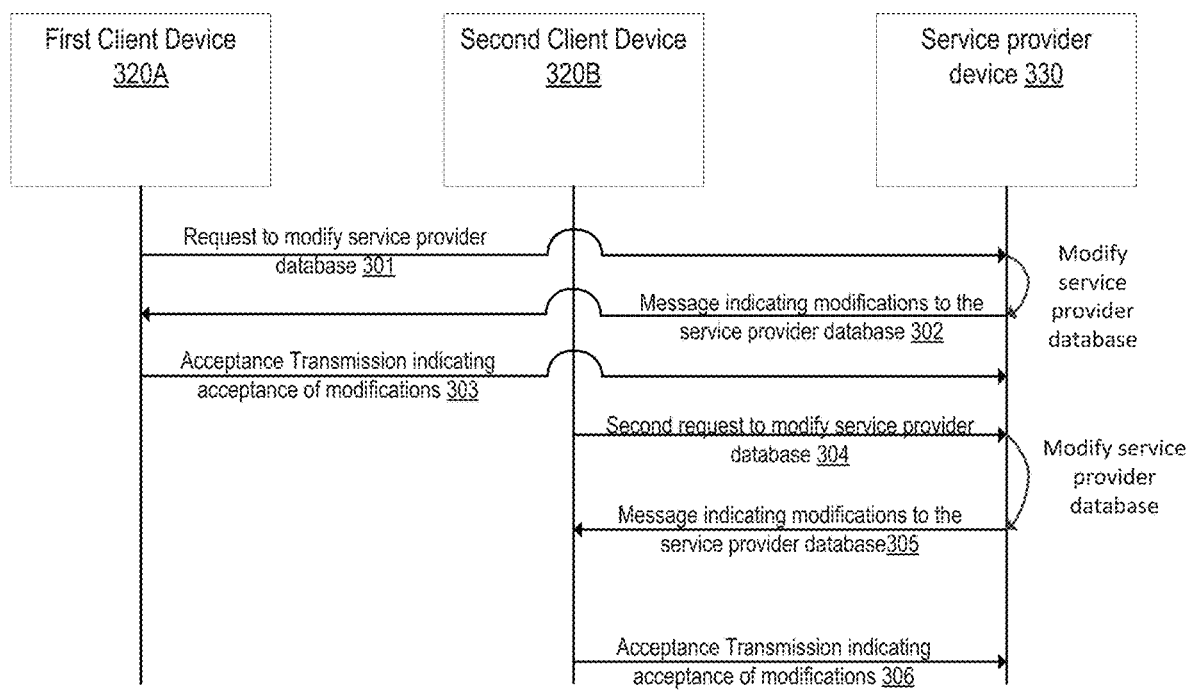
FIG. 3 depicts a signaling process illustrating the communication between multiple client devices and the service provider device.

FIG. 3 depicts a signaling process illustrating the communication between multiple client devices (e.g., 320A, 320B) and the service provider device 330. As shown in FIG. 3, for purposes of illustration, a first client device 320A and a second client device 320B may communicate with the service provider device 330. A client device (e.g., first client device 320A) may include an electronic device as described herein. In some embodiments, any number of client device(s) may communicate with the service provider device 330.

In some embodiments, the first client device 320A may transmit a request 301 to the service provider device 330. The request 301 may represent an instruction for the service provider device to modify a portion of a service provider database. The request 301 may include content that is unknown to the service provider device 330 at the time of receipt, but the request 301 may be interpretable by the service provider device 330.

The request 301 may include information indicative of identifying the first client device 320A, where such information may include client profile information, device identification information, credentials, or other information to identify a client profile associated with a client. In some embodiments, the service provider device 330 may identify a client profile based on identification information included in the request 301.

The request 301 may include information instructing the service provider device 330 to modify a portion of a service provider database. For example, the request may instruct the service provider device 330 to create a new appointment in a calendar database included in the service provider database. Modifying the service provider database is discussed in greater detail with respect to FIG. 4.

The service provider device 330 may communicate a message 302 to the first client device 320A. The message 302 may notify the first client device 320A that the service provider database has been modified based on the request 301. The message 302 may indicate the modification(s) made to the service provider database and an indication that the modifications are complete.

In some embodiments, the message 302 may include instructions for the first client device 320A to transmit a subsequent communication. For example, if the request 301 failed to provide information relating to a suitable time for a new appointment, the service provider device 330 may transmit a message 302 requesting one or more proposed appointment times from the first client device 320A. In this example, the first client device 320A may transmit a subsequent communication indicating a selected proposed appointment time, where a subsequent communication may be an acceptance transmission 303 indicating acceptance of modifications.

As another example, message 302 to the first client device 320A may represent instructions for the first client device 320A to accept modification(s) to the service provider database. The first client device 320A may transmit an acceptance transmission 303 accepting the modification, and the service provider device 330 may modify the service provider database based on receipt of the acceptance transmission 303.

As shown in FIG. 3, a second client device 320B may transmit a second request 304 to the service provider device 330. Request 304 transmitted by second client device 320B may include any or all features of request 301 as discussed above.

Service provider device 330 may receive multiple requests (e.g., request 301, request 304) from multiple client devices (e.g., first client device 320A, second client device 320B). In some embodiments, the requests 301, 304, may include unknown content, where the service provider device 330 may interpret the unknown content of each request 301, 304. Further, service provider device 330 may identify a client profile associated with each request 301, 304 by inspecting the respective request for identification information. In response to each request (e.g., request 301, request 304), the service provider device 330 may transmit a message indicating the modifications to the service provider database based on each request. For example, message 305 may indicate the modifications to the service provider database based on the second request 304.

Figure 4A:
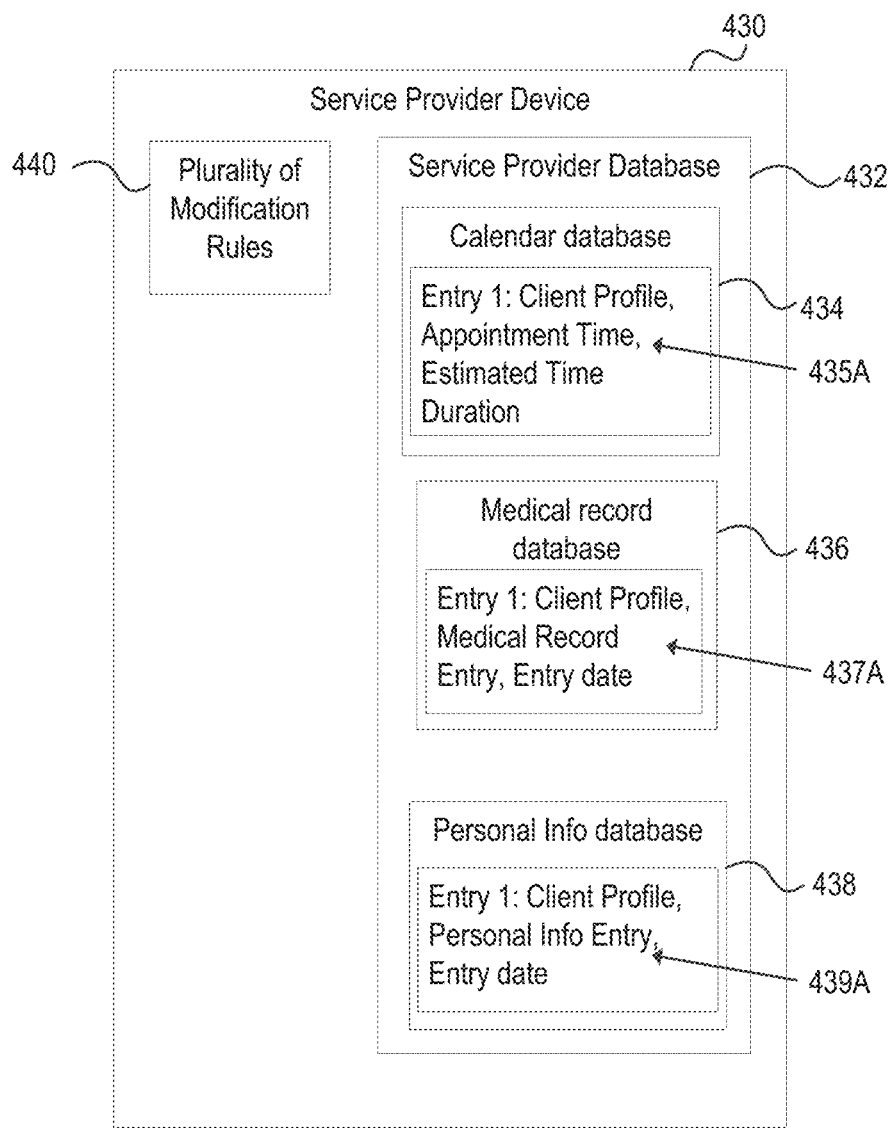
FIG. 4A illustrates the service provider device, consistent with various embodiments.

FIG. 4A illustrates the service provider device 430, consistent with various embodiments. The service provider device 430 may include a computing device, such as a computer, server, or series of interconnected servers. The service provider device 430 may be maintained at a service provider environment, such as a dental office building, hospital, office, etc. In some embodiments, the service provider device 430 is maintained remotely by a remote device and accessible via a network, such as the internet.

As shown in FIG. 4A, service provider device 430 may include a service provider database 432. The service provider database 432 may include a database including data representing a plurality of database entries. A portion of the service provider database 432 may comprise an appointment calendar database 434 (or simply "calendar database 434"). The calendar database 434 may include data representing the upcoming appointments for the service provider. In some embodiments, the calendar database 434 may include a schedule of a plurality of events. The schedule of a plurality of events may be associated with a plurality of clients. In some embodiments, the calendar database 434 are divided into entries, where each entry in the calendar database 434 represents an upcoming appointment or event.

In some embodiments, the calendar database 434 may include a sub-database or folder for each service provider. For example, for a dental office, the calendar database 434 may include a separate sub-database including upcoming appointments for each dentist within the dental office.

As shown in FIG. 4, the calendar database 434 may include at least one entry 435A, where each entry 435A represents an upcoming appointment. An entry 435A may include information such as client profile information, an appointment time, an estimated time duration, etc. Client profile information may include information indicative of a client profile, where a client profile may identify a client such as a client or employee of the service provider. An appointment time may include a scheduled time for the appointment. The estimated time duration may include the estimated time to perform the service.

In some embodiments, entry 435A may include information identifying a prospective service to perform. For example, a prospective service may include performing a root canal dental procedure. The information identifying a prospective service to perform may be provided by a service provider device administrator, such as an employee of the service provider. In some embodiments, an electronic device with a client profile associated with an employee of the service provider may transmit information identifying the service to be performed. In other embodiments, the service provider device may inspect a request transmitted by an electronic device to determine the services to be performed.

Prospective services to be performed may include a corresponding procedure code. A procedure code may include an indicator, such as a number, phrase, code, etc., that indicates the prospective service (or procedure) to be performed. For example, a root canal procedure in a dental office setting may be assigned a first procedure code. Additionally, a cavity filling procedure may be assigned a second procedure code. In some embodiments, all procedure codes and associated procedures may be stored in the service provider device, where the service provider device 430 may determine the procedure to be performed based on a procedure code.

In some embodiments, a procedure code may also be associated with an estimated time duration of the procedure to be performed. The estimated time duration may be based on a historical average time duration of each procedure and/or service provider input as to the time duration.

The service provider database 432 may include a medical record database 436. The medical record database 436 may include one or more entries (entry 437A) representative of medical record information. Medical information may include medical notes, past procedures performed, and other relevant medical information. Medical information may be utilized by a service provider in a medical setting (e.g., dental office, hospital, etc.) for performing medical procedures and making medical diagnoses for a client.

An entry 437A in the medical record database 436 may represent medical information associated with a client. Each entry 437A may include client profile information to identify a client and/or client device. In some embodiments, entries in the medical record database 436 may be sorted by client profile information to allow the service provider device 430 to identify all entries associated with a client profile. In this embodiment, multiple medical record entries may be viewed together in a summary format to allow a service provider (e.g., dentist) to assess all recorded medical information related to a client.

In some embodiments, medical record entries (e.g., entry 437A) may include sensitive and/or confidential data that may be inaccessible to all devices except for authenticated entities, such as the client device and/or the service provider. The service provider device 430 may transmit medical record entries to devices that include credentials associated with authorized client profiles. Client profiles may be authorized by the service provider device 430, or by a service provider administrator. In some embodiments, only client devices with a client profile matching the client profile included on the medical record entry may access the medical record entry.

In some embodiments, medical record entries may be transmitted to another device, such as a third-party service provider device or a client device. To transmit medical record entries to an authorized user, the service provider device 120 may encrypt the medical record entries using a suitable encryption technique, such as RSA, Advanced Encryption Standard (AES), or Triple Data Encryption Standard (3DES), for example. The encrypted medical record entries may be transmitted from the service provider device 120 to another device, such as a client device. The device receiving the encrypted medical record entries may decrypt the encrypted medical record entries using a suitable decryption technique.

The service provider database 432 may include a personal information database 438. The personal information database 438 may include one or more entries (e.g., entry 439A)

representative of personal information. Personal information may include client contact information, personal interests, family members, past residences, etc. Personal information may be utilized by a service provider to provide greater service to the client and to learn more about the client before an appointment. A personal information entry 439A may include client profile information to associate the personal information with a client profile.

In some embodiments, of the calendar appointment entries in the calendar database 434, the medical record database 436 entries, and the personal information database 438 entries may include an entry date. The entry date may indicate the time when the entry was modified and/or recorded in the service provider database 432. A time entry date may be utilized when determining whether information in the service provider database 432 should be updated.

In some embodiments, all or a portion of relevant entries in the service provider database 432 may be viewed in a summary report. A summary report may illustrate a listing of all relevant entries in a single report. For example, a summary report may include all medical record database 436 entries associated with a client profile for a service provider to quickly view the medical information associated with a client. Similarly, as another example, a summary report may include all calendar appointments in the calendar database 434 over an appointment time range, such as all upcoming appointments in a calendar day, for example. The summary report may include all database 432 entries associated with a client profile.

As described above, each record in the service provider database 432 may be associated with a client profile. Further, entries in any of the calendar database 434, medical record database 436, and the personal information database 438 may be associated with a client profile. The service provider device 430 may inspect the service provider database 432 for all entries associated with a client profile upon receipt of a request from a client device that includes information representing the client profile. In some embodiments, the service provider device 430 may modify only the entries associated with the client profile identified in a received request.

The service provider device 430 may parse a request received from a first client device to discover the request to modify the schedule of events in the calendar database 434. In some embodiments, the service provider device 430 may parse the request to identify the client profile and modify an event in the calendar database 434 associated with the identified client profile.

As shown in FIG. 4A, the service provider device 430 may include a plurality of modification rules 440 (or simply "rules"). Each modification rule 440 may represent a set of instructions for modifying a portion of the service provider database 432. For example, a modification rule 440 may instruct the service provider device 430 to add a new entry in the calendar database 434 representing a new appointment. The modification rules 440 and modifying the service provider database 432 based on the modification rules 440 are discussed in greater detail in FIG. 4B.

Figure 4B:
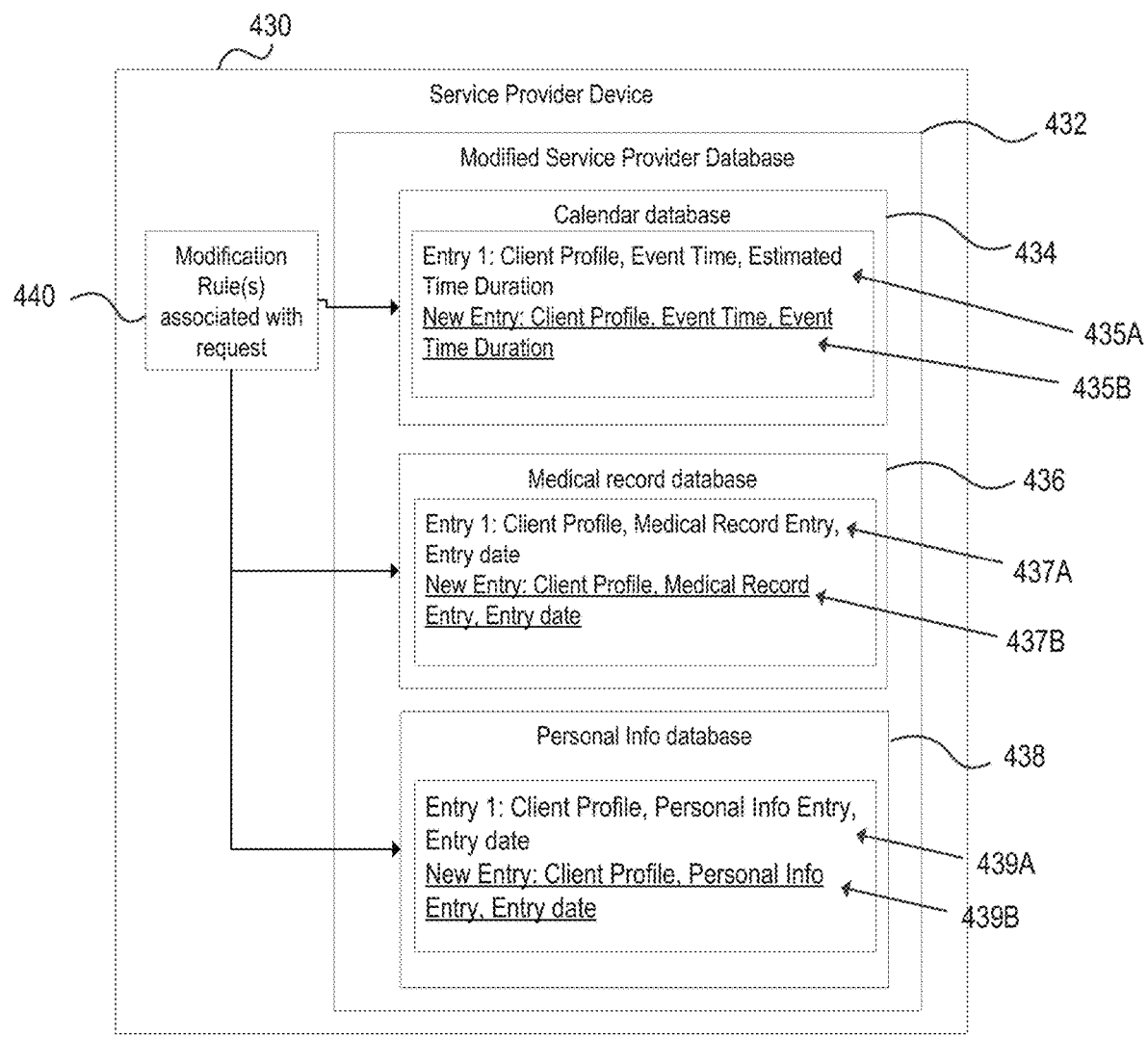
FIG. 4B illustrates a service provider device and a modified service provider database, consistent with various embodiments.

The service provider device 430 may modify a portion of the service provider database 432. FIG. 4B illustrates a service provider device 430 and a modified service provider database 432, consistent with various embodiments.

Service provider device 430 may receive a request from a client device (e.g., first client device 320A as illustrated in FIG. 3). The request may include information indicative of a client profile and information representing the nature of the request. The information representing the nature of the request may include text, words, characters, phrases, etc., indicating any action(s) that the service provider database 432 should take. An example of information representing the nature of the request may include the words 'create new appointment,' where the service provider device 430 may associate these words with a modification rule instructing the service provider device 430 to create a new appointment in the calendar database 434 that includes the client profile associated with the request.

The service provider device 430 may associate the request data (e.g., text) with one or more modification rules. As noted above, each modification rule 440 may instruct the service provider device 430 to modify a portion of the service provider database 432.

In some embodiments, the service provider device 430 may associate the request with modification rules 440 may matching the request text with keywords included in the modification rules 440. Each modification rule 440 may include keywords that are common words used in request text. For example, a modification rule 440 may include a keyword of 'cancel,' where the word 'cancel' may generally represent a request to cancel an appointment in the calendar database 434.

In some embodiments, the service provider device 430 may determine whether the request text matches any keywords included within each modification rule. The service provider device 430 may inspect the request data and keyword data to determine similarities in each set of data. The service provider device 430 may utilize feature extraction, character recognition, text recognition, or another technique to determine similarities between the request data and each keyword.

In some embodiments, the service provider device 430 may develop modification rules based on machine learning. The service provider device 430 may include a plurality of modification rules and discover associations between various terms in the service provider database 432. In other words, the service provider device 430 may discover new connections between words/phrases and modifications to the service provider database 432 based on previous associations between the request text and modification rules 440. In some embodiments, the request text may be associated with modification rules using artificial intelligence, neural networks, or other similar processes.

The request may be formatted using a communication format. A communication format may include a medium through which the message is transmitted. Examples of communication format include text, audio, video, etc. Further, sources of the request (e.g., client device(s)) may transmit requests in various communication format via various communication methods, such as audio in a phone call, text, email, instant message, social media message, etc. The service provider device 430 may identify the communication format of the request by inspecting the request data and/or metadata for indications of the communication channel, or in some embodiments, using text recognition or audio detection to detect the communication format.

The service provider device may receive requests 430, where requests may include various communication format. In some embodiments, the service provider device 430 may convert the communication format of some requests to a desired communication format. Converting some requests into a uniform communication format may increase recognition accuracy of the request data. Any communication format may be the uniform communication format and converting requests to a desired communication format may make all requests a uniform communication format. In an embodiment, for purposes of illustration, text may be the desired communication format.

In some embodiments, converting the request into the uniform communication format may include transcribing an audio request into text. The service provider device 430 may transcribe a request including an audio communication format by transcribing the audio into text using a technique such as quick transcription (QTR), quick-rich transcription (QRTR), careful transcription (CTR), or another similar transcription technique.

As shown in FIG. 4B, a modification rule may instruct the service provider device 430 be to add a new entry (or appointment) 435B to the calendar database 434. To illustrate the updated calendar database 434, new entry 435B is underlined. In some embodiments, the service provider device 430 may inspect the calendar database 434 for an available appointment time, where an available appointment time is a portion of the calendar database 434 where there is no presently scheduled appointment. The request may include information indicating a preferred appointment time for the proposed appointment, and the service provider device 430 may inspect the calendar database 434 for an available appointment time at or near the preferred appointment time for the proposed appointment.

To prevent double-booking of an available appointment time, the service provider device 430 may inspect the calendar database 434 for an available appointment time that is equal to or greater than the estimated time duration of the services to be performed in the proposed appointment. If the service provider device 430 identifies a suitable available appointment time, the service provider device 430 may add the proposed appointment to the calendar database at the available appointment time.

A modification rule 440 may instruct the service provider device 430 to modify a pending appointment in the calendar database 434. Modifying a pending event (e.g., entry 435A) may include replacing the appointment time of the pending appointment to a second appointment time. To modify a pending appointment, the service provider device 430 may inspect the calendar database 434 for an available appointment time. The second appointment time may be greater or equal to the estimated time duration of the pending appointment. The service provider device 430 may communicate a transmission indicating that one or more available appointment times are available to modify the pending appointment to one of the available appointment times.

A modification rule 440 may instruct the service provider device 430 to cancel a pending appointment in the calendar database 434. The pending appointment that is cancelled may be referred to as a cancelled appointment. The service provider device 430 may remove the pending appointment from the calendar database 434. After cancelling the pending appointment, the appointment time of the cancelled appointment may be shown in the calendar database as an available appointment time. The service provider device 430 may determine whether an upcoming appointment or a potential appointment could be moved into the appointment time of the cancelled appointment.

A modification rule 440 may instruct the service provider device 430 to modify generate or modify a medical record entry in the medical record database 436. The medical record database 436 may include one or more medical record entries, where each medical record entry is associated with a member. Each medical record entry may include medical information, such as previous medical procedures, a previous medical diagnosis, and other medical professional notes/advice. Medical record entries may be treated as confidential, as medical record information is generally confidential in nature and may require certain protections to maintain the privacy of the medical information. The medical record entry may be transmitted or accessed only by authorized users and/or entities. Transmitting any medical record entry may include encrypting the medical record data and/or transmitting the data over an encrypted network using a suitable encryption technique.

Generating a new medical record entry may include inspecting the request for modification rule(s) 440 that indicate adding a new medical record entry. A modification rule 440 may include adding a medical record entry with medical information provided in the request. The service provider device 430 may identify medical information using a suitable text recognition technique. The service provider device 430 may utilize natural language processing to generate a medical record entry with narrative language that may be easily understood by a service provider. Each medical record entry may include client profile information to associate each medical record entry with a client.

A modification rule 440 may instruct the service provider device 430 to generate or modify a personal information entry in the personal information database 438. Personal information entries may include personal information of a member, such as contact information or family information, for example. Generating a personal information entry may include inspecting the request for modification rules that include generating a personal information entry. The service provider device 430 may inspect the request for personal information and add the personal information into the personal information entry. The service provider device 430 may utilize natural language processing to generate a personal information entry with narrative language that may be easily understood by a service provider. The personal information entry may include information indicating a member's favorite song and/or movie, where the song/movie may be played during a member event.

The service provider device 430 may transmit a message to a client device indicating the modification(s) to the service provider database 432 based on the request. The service provider device 430 may transmit the message to the client device associated with the client profile identified in the request. In some embodiments, the message to the client device may include a request for acceptance of the modification(s) to the service provider database 432.

FIG. 5 illustrates a flow diagram illustrating a method to maintain a service provider database, consistent with various embodiments. The method may include, at block 502, receiving a request to modify a service provider database from a client device a first communication in one of a plurality of communication formats, the first communication including unknown content that is interpretable by the service provider device. The request may include data indicative of a client profile to identify a client, such as a client or employee of a service provider. The request may also include data identifying instructions to modify a portion of the service provider database. One or more requests may be received by the service provider device. The service provider device may access and modify the service provider database.

In some embodiments, the service provider device may receive a second request from a second client device. The service provider device may receive a plurality of requests from a plurality of client devices. The service provider device may identify a client profile, and/or a client device associated with each request and modify the service provider database based on each request. The service provider database may be configured to receive, track, and modify the service provider database according to each request received. This may allow for the service provider device to accurately modify the service provider database with greater accuracy and efficiency.

In some embodiments, the service provider database includes a calendar database that includes one or more appointment entries associated with the client device, a medical records database that includes one or more medical records entries associated with the client device, and a personal information database that includes personal information entries associated with the client device.

In some embodiments, the service provider device may inspect the request for information indicative of the client device. Such information may include information to identify a client profile associated with a client, or information identifying a device associated with a client. The service provider device may compare the information with known identification information to identify the client device and/or the client profile.

In some embodiments, the client device includes a mobile phone, and the request is transmitted by a mobile application executing on the mobile phone.

The method may include, at block 504, parsing the first communication to discover a request from a first client to modify a schedule of a plurality of events stored in the service provider database, the schedule being associated with a plurality of clients including the first client. Parsing the first communication may include determining characters and text from the request data and metadata. The service provider device may parse the first communication using a suitable text recognition technique as described herein.

In some embodiments, the service provider device may identify a communication format of the request, where the communication format is a mode of communication that comprises the information transmitted in the request. Example communication formats may include text, audio, etc.

In some embodiments, the service provider device may receive a second request that includes a second communication channel. The service provider device may determine that the second communication channel is different than the first communication channel. In response, the service provider device may convert the second communication channel to the first communication channel based on determining the second communication channel is different than the first communication channel. This may ensure uniformity of communication channels for each request received.

The method may include, at block 506, modifying the schedule in accordance with the request based on a rule of a plurality of rules that matches the request responsive to discovering the request.

The method may include, at block 508, sending a second communication in one of the plurality of communication formats selected based on association with the client in the service provider database, the second communication indicating that the schedule has been modified in accordance with the request or seeking information required to complete the modification.

In some embodiments, the service provider device may inspect the service provider database for any entries associated with a client profile that corresponds to a request. All such entries may be associated with a client of the service provider. The service provider device may modify any entries associated with the client profile. Identifying all entries associated with the client profile may allow for the service provider device to identify and modify the service provider database with greater accuracy and efficiency.

In some embodiments, the service provider device may determine whether the text identified in a request matches any keywords, where each keyword is associated with a modification rule. Matching the request text with keywords may be performed using a technique such as text recognition, character extraction, etc. The service provider device may modify the service provider database based on the keywords that match the text identified within the request.

Calendar Database Management Overview

Service providers generally maintain a listing of upcoming appointments in an electronic calendar, where each appointment is associated with a client. For a variety of reasons, however, scheduled appointments are missed and/or cancelled by clients. Generally, to indicate an intent to cancel an upcoming appointment, the client may contact the service provider through one of a variety of communication formats, such as in person, phone, email, etc. Service providers, in response to such a communication to cancel an appointment, may attempt to find a replacement appointment to update the now-cancelled appointment time with new client information.

Generally, to update a cancelled appointment time to include new client information, a service provider may interact with potential client(s) about the available appointment time. This interaction may include an invitation to schedule and/or reschedule an appointment to the available appointment time. Scheduling appointments into available appointment times may increase utilization of the service provider resources, which may lead to increased efficiency and utilization of the service provider. Therefore, service providers may attempt to update cancelled appointment times in the calendar with a replacement client before the cancelled appointment time has passed.

Figure 6:
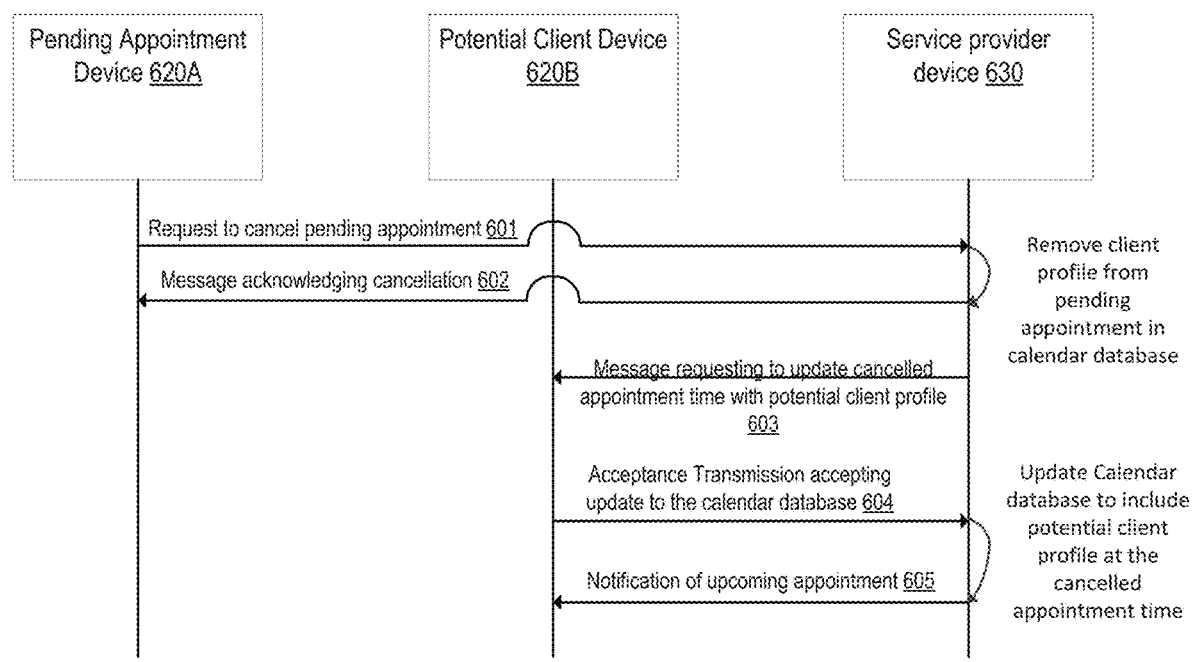
FIG. 6 depicts a signaling process illustrating the communication between devices and a service provider device.

FIG. 6 depicts a signaling process illustrating the communication between devices and a service provider device 630. A pending appointment device 620A may include an electronic device associated with a client profile, where the client profile is associated with a pending appointment. Each calendar appointment in the calendar database may include client profile information to identify a client profile associated with an appointment. In some embodiments, a client profile may indicate a client of the service provider.

As shown in FIG. 6, the pending appointment device 620A may transmit a request 601 to cancel a pending appointment to the service provider device 630. The request 601 may include information identifying the client profile, such as credentials, a username, number, code, or other similar identifying information. The service provider device 630 may include a registry of all client profiles and associated identification information to identify the client profile from the request.

Based on the client profile determined from the request 601, the service provider device 630 may inspect a calendar database to identify an upcoming appointment including the client profile information. In some embodiments, the calendar database may be included in a service provider database that includes a plurality of upcoming appointments, where each appointment is associated with a client profile.

The request 601 may contain unknown content that may be interpretable by the service provider device 630. The service provider device 630 may determine that request 601 is instructing the service provider device 630 to cancel an upcoming/pending appointment by associating the request 601 with one or more modification rules. Associating the request with modification rules is discussed in greater detail below.

The service provider device 630 may cancel an upcoming appointment associated with the client profile by removing the client profile information from the appointment time. The service provider device 630 may modify the appointment time to indicate that the appointment time is available to be updated with another client profile.

In some embodiments, the service provide device 630 may transmit a message 602 to pending appointment device 620A acknowledging the receipt of the request 601 and verifying the completion of the request to cancel the pending appointment. The message 602 may include information indicating the modification(s) made to the calendar database.

In some embodiments, the message 602 may include one or more prospective times for a replacement appointment time. This may allow for the pending appointment device 620A to reschedule their now-cancelled appointment at a replacement appointment time. Each prospective time may include a time that is available (e.g., not currently associated with a client profile of another client). The service provider device 630 may determine prospective times based on inspecting available appointment times that have a time duration less than or equal to the estimated time duration of the replacement appointment. The pending appointment device 620A may transmit an acceptance message indicating a selected prospective time. In response, the service provider device 630 may update the service provider database to add the replacement appointment associated with the client profile at the prospective appointment time.

The service provider may attempt to update a cancelled appointment time in the database by inviting a potential client to provide an acceptance transmission to have client profile information updated to the cancelled appointment time. A potential client device 620B may be a device associated with a prospective client with an intent to schedule an upcoming appointment, or in some embodiments, a potential client may include a client with a previously-scheduled appointment that may replace the previously-scheduled appointment time to the now-cancelled appointment time. Updating a cancelled appointment time with a potential client profile may increase efficiency and utilization of the service provider resources.

The service provider device 630 may determine a suitable potential client by inspecting a listing of potential clients accessible to the service provider device 630. Determining suitable potential clients is discussed in greater detail below. A potential client may be associated with a potential client profile, where a potential client profile includes information indicative of the potential client and/or a potential client device 620B. Potential client profile information may include credentials, a username, code, number, or other information to identify a potential client. In some embodiments, the potential client profile information may include a serial number, MAC address, license key, mobile phone number, or other information to identify a device associated with a potential client profile. Potential client profiles and associated data may be stored in a registry accessible to the service provider device 630.

The service provider device 630 may transmit a message 603 to a potential client device 620B requesting to fill a cancelled appointment. Message 603 may be transmitted to one or more potential client devices 620B. A potential client device 620B may transmit an acceptance transmission 604 indicating an acceptance to add the potential client profile information to the cancelled appointment time. The acceptance transmission 604 may indicate an acceptance for the potential client to attend an appointment at the available appointment time.

Based on the acceptance transmission 604, the service provider device 630 may update the calendar database to include the potential client profile information to the cancelled appointment time. This may prevent double-booking a cancelled appointment time with multiple potential client profiles. In some embodiments, the service provider device 630 may remove potential client profile information associated with a previously-scheduled appointment, as the potential client may have agreed to replace the previously-scheduled appointment time with the cancelled appointment time.

The service provider device 630 may transmit a notification of the upcoming appointment 605 to the potential client device 620B. This notification 605 may indicate the addition of the appointment at the cancelled appointment time. The notification 605 may also represent a reminder to the potential client to attend the upcoming appointment.

Figure 7A:
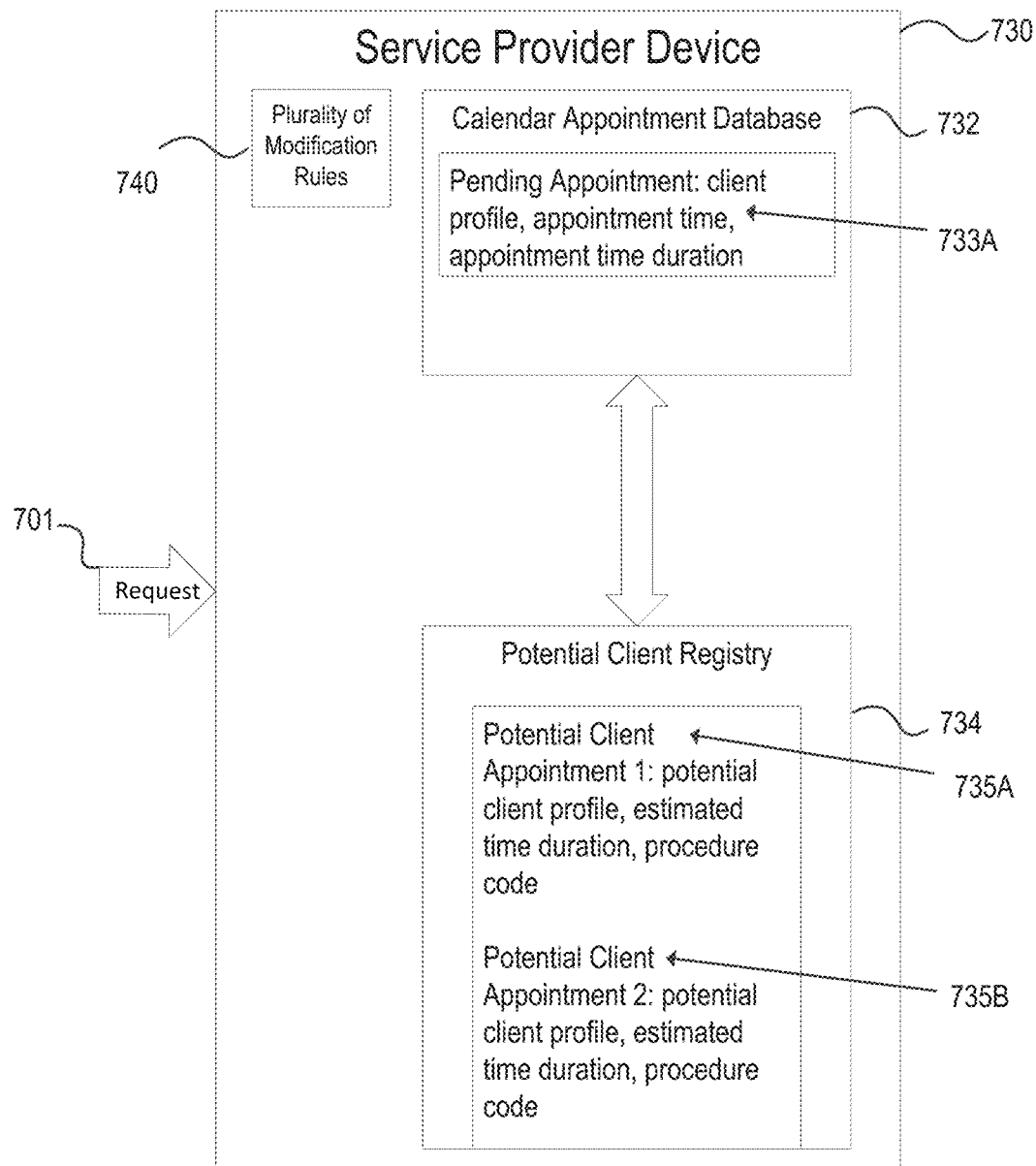
FIG. 7A illustrates a service provider device, consistent with various embodiments.

FIG. 7A illustrates a service provider device 730, consistent with various embodiments. The service provider device 730 may access a calendar appointment database 732. The calendar appointment database 732 may include database information representing upcoming appointments at various appointment times. In some embodiments, the calendar database 732 may include one or more events (e.g., pending appointment 733A) that are part of a plurality of events. For example, the calendar appointment database 732 may include a pending appointment 733A that represents an upcoming scheduled appointment associated with a client.

As shown in FIG. 7A, an appointment (e.g., pending appointment 733A) may include an appointment time. The appointment time may include the scheduled time for the appointment, where all appointments in the calendar appointment database 732 may be scheduled chronologically by appointment time.

In some embodiments, each appointment may include client profile information. The client profile information may include information indicative of a client, such as a client of the service provider, for example. In some embodiments, pending appointment 733A may include client profile information to indicate that the appointment time has been occupied or scheduled. In other embodiments, an available appointment time, such as an appointment time that was cancelled, may not include any client profile identification to indicate an available appointment time.

As shown in FIG. 7A, an appointment (e.g., pending appointment 733A) may include an appointment time duration. The appointment time duration may include the estimated time duration to perform the service. In some embodiments, each appointment time duration may be fixed, i.e. each appointment time duration is a predetermine time, such as 30 minutes, 1 hour, etc. In other embodiments, the appointment time duration may include the estimated time to perform a service, which may be estimated by one of the service provider or the service provider device 730.

In some embodiments, pending appointment 733A may include information identifying a prospective service to perform. For example, a prospective service for the entry may include performing a root canal dental procedure. The information identifying a prospective service to perform may be provided by a service provider device administrator, such as an employee of the service provider. In some embodiments, a client device including a client profile associated with an employee of the service provider may transmit information identifying the service to be performed.

In other embodiments, the service provider device 730 may inspect a request transmitted by pending appointment client device (e.g., pending appointment device 620A of FIG. 6) to determine the services to be performed.

Prospective services to be performed may include a corresponding procedure code. A procedure code may include an indicator, such a number, phrase, code, etc., that may indicate the prospective service (or procedure) to be performed. For example, a root canal procedure in a dental office setting may be assigned a first procedure code. Additionally, a second dental procedure may be assigned a second procedure code. In some embodiments, all procedure codes and associated procedures may be stored at the service provider device 630, where the service provider device 630 may determine a procedure based on a procedure code.

In some embodiments, a procedure code may be associated with an appointment time duration of the procedure to be performed. The appointment time duration may be based on a historical average time duration of each procedure and/or service provider input as to the time duration.

As shown in FIG. 7A, the service provider device 730 may include a potential client registry 734. The potential client registry 734 may include a listing of potential client appointments (e.g., 735A, 735B). For purposes of illustration, a first potential client appointment 735A and a second potential client appointment 735B are shown. However, any number of potential client appointments may be listed in the potential client registry 734. In some embodiments, the potential client registry 734 may be referred to as a potential client listing 734.

The potential client registry 734 may include potential client profiles associated with each potential client appointment. A potential client profile may be information indicative of a potential client. Potential clients may include clients who are prospective clients and may schedule an upcoming appointment in the calendar appointment database 732. In some embodiments, potential clients may include clients that have scheduled/upcoming appointment(s) and may move the appointment time to an available appointment time.

In some embodiments, a potential client appointment may include an estimated time duration. The estimated time duration may include a projected or estimated time to complete the services. The estimated time duration may be automatically generated based on the procedure to be performed. In some embodiments, the estimated time duration may include the time provided by a service provider to perform the services. The potential client appointment may include a procedure code as discussed above. The procedure code may be associated with an estimated time duration, and the service provider device 730 may inspect the procedure code to determine the estimated time duration.

As shown in FIG. 7A, the service provider device 730 may include a plurality of modification rules 740. Each modification rule 740 may represent instructions to modify a portion of the calendar appointment database 734. In an example, a modification rule 740 can include an instruction to cancel a pending appointment associated with a client profile.

Figure 7B:
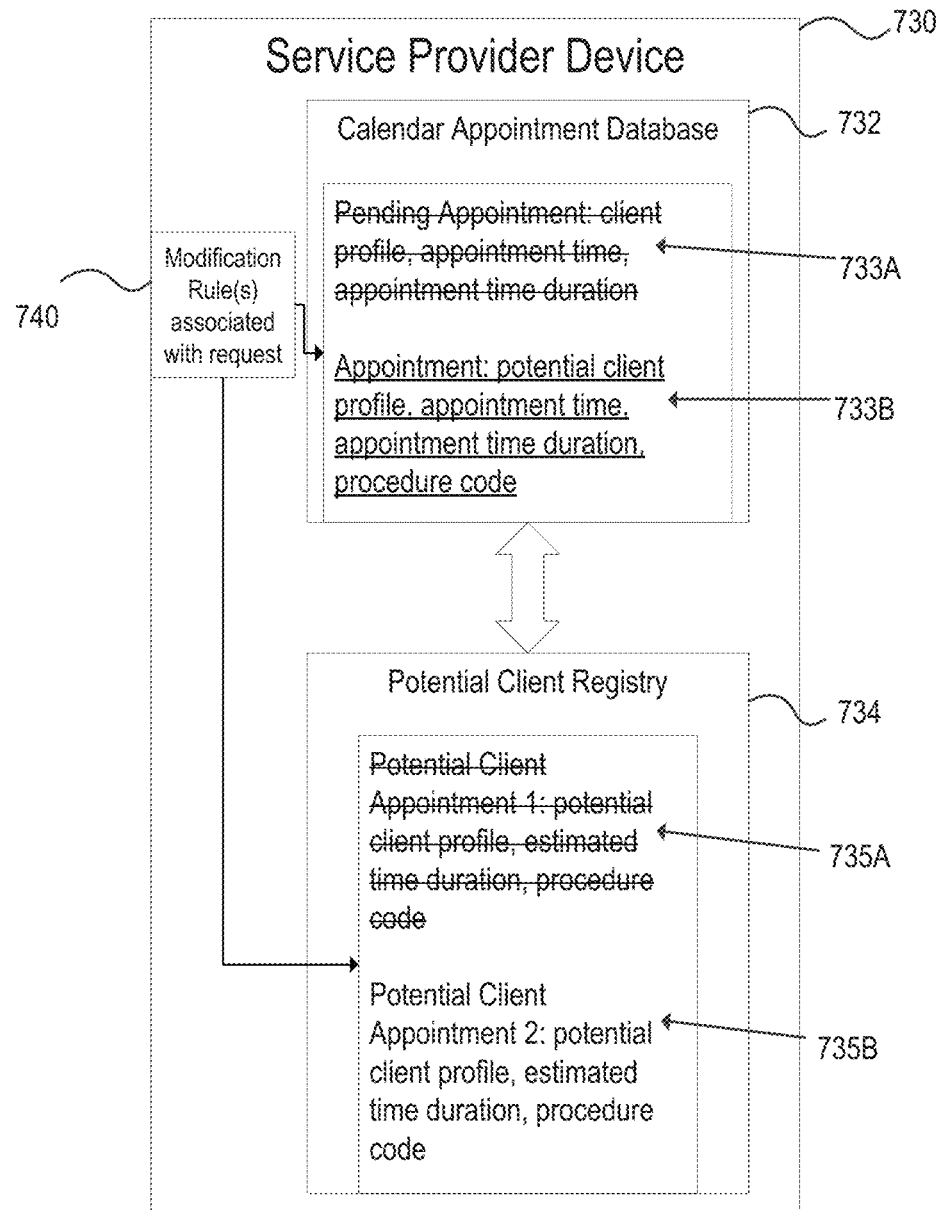
FIG. 7B illustrates a service provider device and a modified calendar appointment database, consistent with various embodiments.

FIG. 7B illustrates a service provider device 730 and a modified calendar appointment database 732, consistent with various embodiments. As shown in FIG. 7B, the calendar appointment database 732 may be modified. The service provider device 730 may inspect request data to associate the request with one of a plurality of modification rules 740. As noted above, each modification rule 740 may instruct the service provider device 730 to modify a portion of the calendar appointment database 732.

The service provider device 730 may parse a communication (e.g., request 601 of FIG. 6) to discover a request to modify an event associated with a client. In some embodiments, such parsing may include matching the request text with keywords included in modification rules 740. Each modification rule 740 may include keywords that are likely words used in request text. For example, a modification rule 740 may include a keyword of 'cancel,' where the word 'cancel' may generally represent a request to cancel an appointment in the calendar database 734.

The service provider device 730 may determine whether the request text matches any keywords included within each modification rule. The service provider device 730 may inspect the request data and keyword data to determine similarities in each set of data. The service provider device 730 may utilize feature extraction, character recognition, text recognition, or another technique to determine similarities between the request data and each keyword.

In some embodiments, the service provider device 730 may develop modification rules 740 based on machine learning. The service provider device 730 may include a plurality of modification rules 740 and discover associations between various terms in the calendar database 732. In other words, the service provider device 730 may discover new connections between words/phrases and modifications to the calendar database 732 based on previous associations between the request text and modification rules 740. In some embodiments, the request text may be associated with modification rules using artificial intelligence, neural networks, or other similar processes.

The modification rule(s) 740 may instruct the service provider device 730 to remove client profile information associated with a pending appointment (e.g., pending appointment 733A). The service provider device 730 may remove and client profile information from the pending appointment and indicate that the pending appointment time is available for a replacement appointment.

In some embodiments, the service provider device 730 may create a hierarchy to update client profile information for each available appointment time. The service provider device 740 may use factors, such as time duration, the day/time of the appointment, and the potential to fill the appointment to create the hierarchy. The hierarchy created by the service provider device 730 may rate each available appointment time by importance to be updated. Accordingly, the service provider device 730 may first attempt to update available appointment times that include a greater importance in the hierarchy to optimize database updating and service provider utilization.

The service provider device 730 may update the now-cancelled pending appointment 733A to comprise information from a potential client appointment 735A into appointment 733B. The modification rule(s) 740 may represent an instruction to the service provider device 730 to inspect the potential client appointments (e.g., potential client appointment 735A, 735B) in the potential client registry 734 to determine suitable potential client appointments. In some embodiments, the service provider device 730 may determine whether each potential client appointment includes an estimated time duration that is less than or equal to the appointment time duration of the now-cancelled appointment time. This may filter the potential client appointment to such appointments that may fit within the time duration of the available time. In some embodiments, each potential client appointment may include appointment time preference information indicative of the preferred time for the potential client appointment. In some embodiments, the service provider device 730 may rank each potential client appointment by procedure code, where the most desired procedure codes are ranked highest.

In some embodiments, the service provider device 730 may identify several suitable potential client appointments to be replaced at the now-cancelled appointment time. In some embodiments, the service provider device 730 may transmit a message to a potential client device associated with a potential client profile, where the potential client profile corresponds with a chosen potential client appointment. The message may indicate a response from the potential client device to accept the request to fill the cancelled appointment time. In some embodiments, the service provider device 730 may transmit the message to multiple potential client devices. The first potential client device to transmit an acceptance message accepting the invitation to fill the cancelled appointment time may receive the appointment at the cancelled appointment time. The service provider device 730 may update the calendar database 732 to include the potential client appointment at the appointment time, as shown in 733B of FIG. 7B.

As shown in FIG. 7B, after a potential client appointment (e.g., 735A) has transmitted an acceptance transmission to the service provider device 730, the service provider device 730 may remove the potential client appointment from the potential client registry 734. For example, potential client appointment 735A may be removed from the potential client registry 734. Removing the potential client appointment from the potential client registry may include disassociating any potential client profile information from a listing of the potential client registry 734 associated with a potential client appointment.

In some embodiments, after a potential client appointment (e.g., 735A) has transmitted an acceptance transmission to the service provider device 730, the service provider device 730 may add the potential client appointment to the calendar database 732. Adding the potential client appointment to the calendar database 732 may represent updating the calendar database 732 to replace the available appointment time with a potential client profile associated with a potential client.

Figure 8:
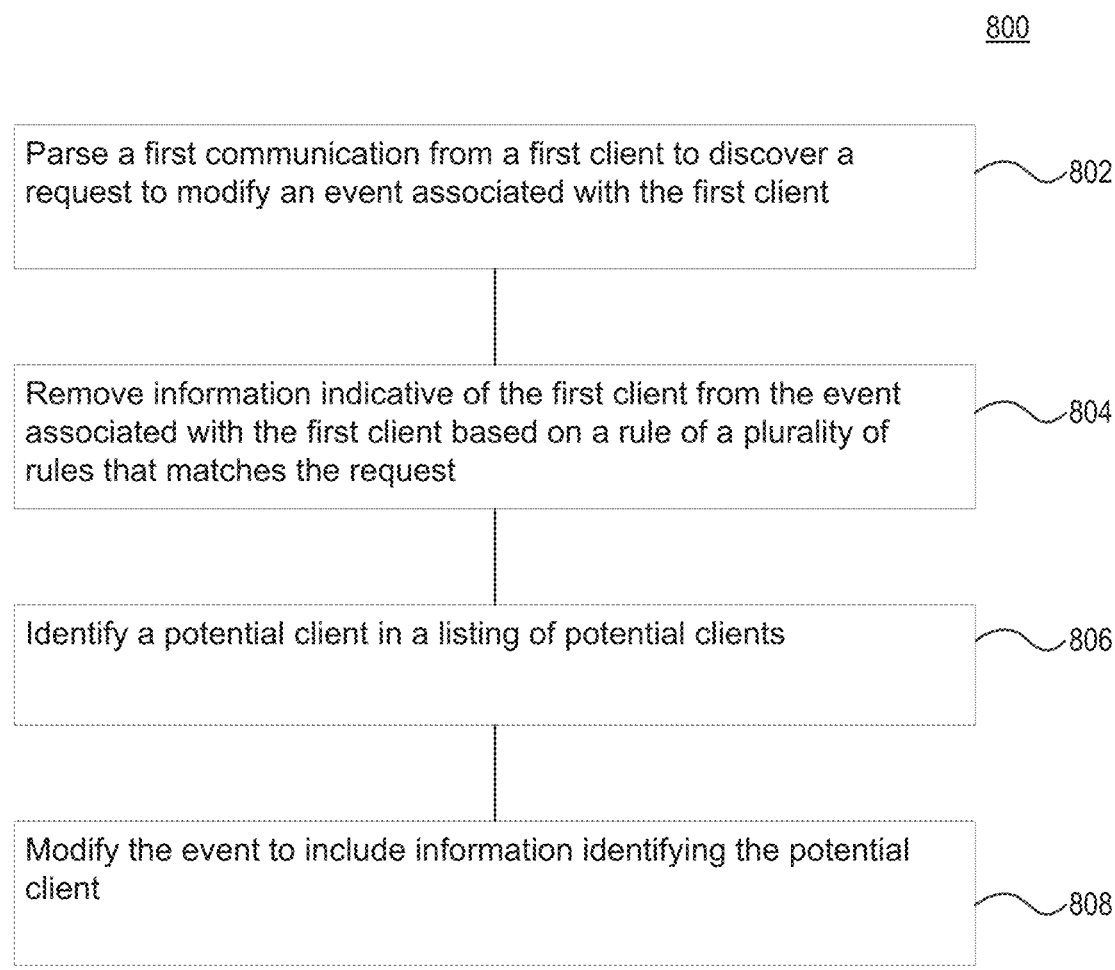
FIG. 8 illustrates a flow diagram illustrating a method to maintain a service provider database, consistent with various embodiments.

FIG. 8 illustrates a flow diagram illustrating a method performed by a service provider device to modify a service provider database. The method includes, at block 802, parsing a first communication from a first client to discover a request to modify an event associated with the first client. An event may be part of a schedule of a plurality of events stored in the service provider database. The schedule may be associated with a plurality of clients including the first client.

In some embodiments, the first communication is one of a plurality of communication formats, the first communication including unknown content that is interpretable by the service provider device. Such communication formats may include a text-based format and an audio-based format.

The method includes, at 804, removing information indicative of the first client from the event associated with the first client based on a rule of a plurality of rules that matches the request. The service provider device may remove said information responsive to discovering the request.

The method includes, at 806, identifying a potential client in a listing of potential clients. The potential client may accept a proposed scheduling to update the event to include information identifying the potential client in a second communication.

The method includes, at 808, modifying the event to include information identifying the potential client. Said modifying may occur upon receiving the second communication from the potential client indicating an acceptance of proposed scheduling.

In some embodiments, a third communication may be transmitted to the potential client indicating that the event has been modified to include information identifying the potential client.

In some embodiments, a fourth communication is transmitted to a plurality of potential clients of the potential client listing. Upon receiving a fifth communication from one of the plurality of potential clients indicating an acceptance of proposed scheduling, the service provider device may modify the event to include information identifying the one of the plurality of potential clients.

In some embodiments, a sixth communication is received at the service provider device from a second client. The service provider device may identify a communication format of the sixth communication and determine whether the communication format of the first communication matches the communication format of the sixth communication. The service provider device may convert the sixth communication to the communication format of the first communication based on determining the communication format of the sixth communication does not match the communication format of the first communication.

Dynamic Communication System Overview

Service providers generally have one or more employees perform services for clients. For example, a dental office may employ a dentist and staff members to perform dental procedures for clients. In many service provider environments, employees may move about the environment to perform tasks. In a dental office, for example, a dentist may move about the dental office environment to perform dental procedures for clients. Additionally, in such service provider environments, many employees of the service provider may move about the environment to perform tasks assigned to each employee.

However, many service providers operate in environments (e.g., hospital, dental office, etc.) with large campuses and include many employees. Accordingly, determining the location of an employee and requesting the employee to perform a task in such environments may require great service provider resources.

In many service provider environments (e.g., hospital, dental office, etc.), employees of the service provider may perform services in a time-sensitive manner. For example, in a dental office environment, a dentist may have to meet with a client in a specific area of the environment, such as a waiting room, for example. In another example, in a hospital environment, a nurse may be asked to assist with a surgical procedure in a specific room within the hospital environment. In some embodiments, the service provider may divide tasks by group, where members of each group in a service provider setting may perform a set of tasks. Examples of groups may include, for example, doctors, nurses, and support staff in a hospital environment.

Conventional systems may include a device associated with each employee of a service provider. Each device may be connected to a network, where the devices may receive communications indicating a request for an employee to perform a task. In some embodiments, all devices in a service provider environment may receive a communication indicating a request for assistance within the service provider environment. In these embodiments, however, many devices receiving such communications may lead to inefficient service provider operations, as many communications may inundate an employee with communications that are not relevant to the employee. Further, if an employee receiving a communication is not within a close geographical proximity to the desired location in the communication, the employee may not be capable of responding to the communication.

In some embodiments, a specific device associated with an employee may receive a targeted communication to perform a task. However, in many cases, the employee receiving the targeted communication may be unavailable to perform the task, as the employee may be located outside of a range of the desired location to perform the task.

A communication system to forward a communication is disclosed. The dynamic communication system may determine a geographic location and a task group of each electronic device in an environment. A service provider device may identify a first location and a first task group based on a communication, where the first location is the desired location to perform a task and the first task group is a group of employees that may perform the task. The service provider device may forward the communication to all electronic devices associated with the first task group and are within a threshold proximity of the first location.

Selectively forwarding a communication to electronic device(s) associated with individuals, such as employees of a service provider, may increase efficiency of the service provider device and the communication environment. In some embodiments, forwarding the communication to some electronic device(s) based on geographic location and task group may target the communication to relevant individuals that may respond to the communication.

Figure 9:
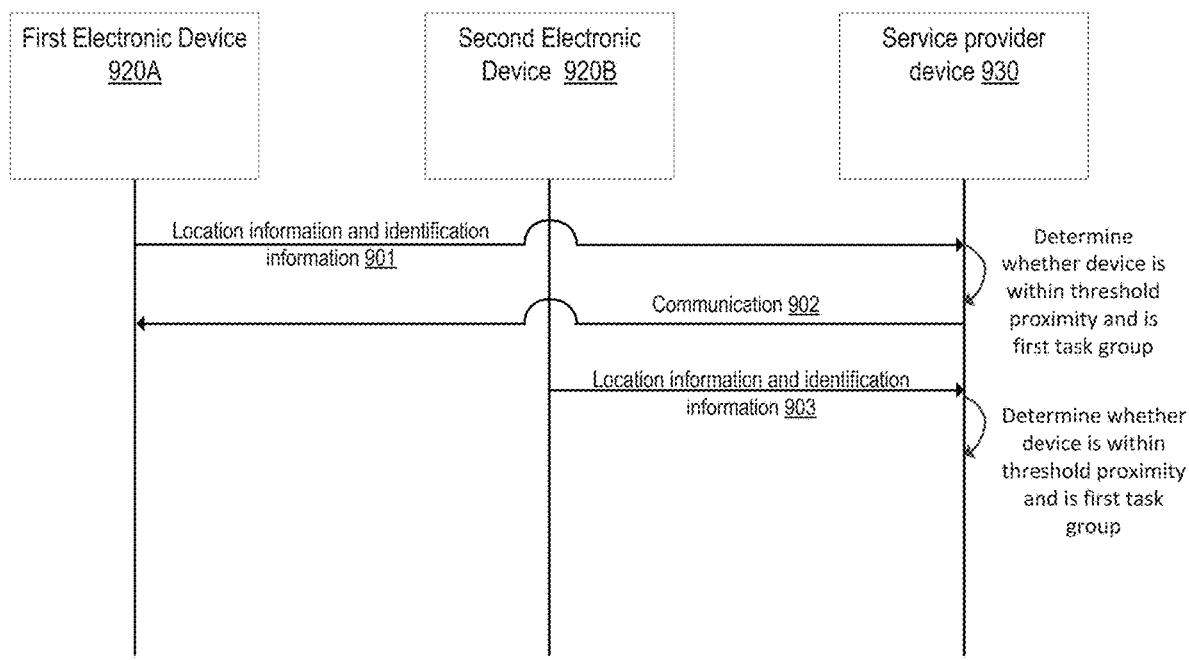
FIG. 9 illustrates a signaling process between electronic devices and a service provider device 930.

FIG. 9 illustrates a signaling process between electronic devices and a service provider device 930. For purposes of illustration, as seen in FIG. 9, a first electronic device 920A and a second electronic device 920B are in communication with the service provider device 930. However, any number of electronic devices may be in communication with the service provider device 930.

A first electronic device 920A may transmit location information and identification information 901 to the service provider device 930. Location information may represent information indicative of a geographic location of the electronic device. In some embodiments, location information may include cellular connectivity data (e.g., cell site location information (CSLI)) and/or space satellite connectivity data (e.g., global positioning system (GPS) information). The location data may be used to triangulate the geographic position of the electronic device within a network (e.g., a wireless cellular network). The electronic device may include an Internet Protocol (IP) address associated with a network, where the IP address may include geotagging data or metadata that may be inspected to determine the geographic location of the electronic device.

Identification information may include information to identify the electronic device (e.g., first electronic device 920A) and/or the individual associated with the electronic device. Identification information may also be referred to as client profile information, where a client profile may include information indicative of identifying a client, such as an employee of a service provider. Examples of client profile information may include credentials, client name, a username and password, a unique code, etc. In some embodiments, the client profile may include device identification information to identify an electronic device associated with the client. Such device identification information may include, for example, a device serial number, MAC address, internet protocol (IP) address, or a license key.

The service provider device 930 may store a plurality of client profiles and associated identification information, where each client profile may be unique to a client. In some embodiments, the service provider platform 202 may include a client profile registry that includes the client profiles and associated identification information and/or device identification information to identify a client and/or client device.

In some embodiments, the identification information may include task group information identifying a task group of the identified client profile. A task group may include a group of individuals within the service provider environment that are permitted to perform a task or set of tasks. A client profile may be divided into one or more task groups. For example, in a dental office environment, dentists may comprise a first task group, and support staff comprise a second task group.

The service provider device 930 may determine the location and the task group of each electronic device based on the information received at the service provider device 930. This determination is discussed in greater detail in FIG. 10. Based on this determination, the service provider device 930 may transmit the communication to some electronic devices. In the embodiment as illustrated in FIG. 9, the first electronic device 920A receives communication 902. To transmit the communication 902, the service provider device 930 may determine that the first electronic device 920A is within a threshold proximity of the first location and is included in the first task group.

In some embodiments, a second electronic device 920B may transmit location information and identification information 903 to the service provider device 930. The service provider device 930 may determine whether the second electronic device 920B is within the threshold proximity and is included in the first task group using any of the techniques as described above. However, in the embodiment as illustrated in FIG. 9, the service provider device 930 does not transmit a communication to the second electronic device 920B.

In some embodiments, the service provider device 930 may selectively transmit communication 902 to one or more electronic devices (e.g., first electronic device 920A). The communication 902 may be transmitted to electronic device(s) based on the geographic location and the task group identified with each device. Selectively transmitting the communication 902 may ensure that only relevant individual(s) associated with electronic device(s) receive the message. In other words, individuals in the service provider environment who are beyond the relevant geographic location threshold distance and/or are not equipped to perform the task required in the communication may not receive the communication. Targeted transmission of the communication may increase service provider device efficiency, as communication resources are reserved by transmitting the communication only to relevant electronic devices, rather than to all electronic devices.

Figure 10:
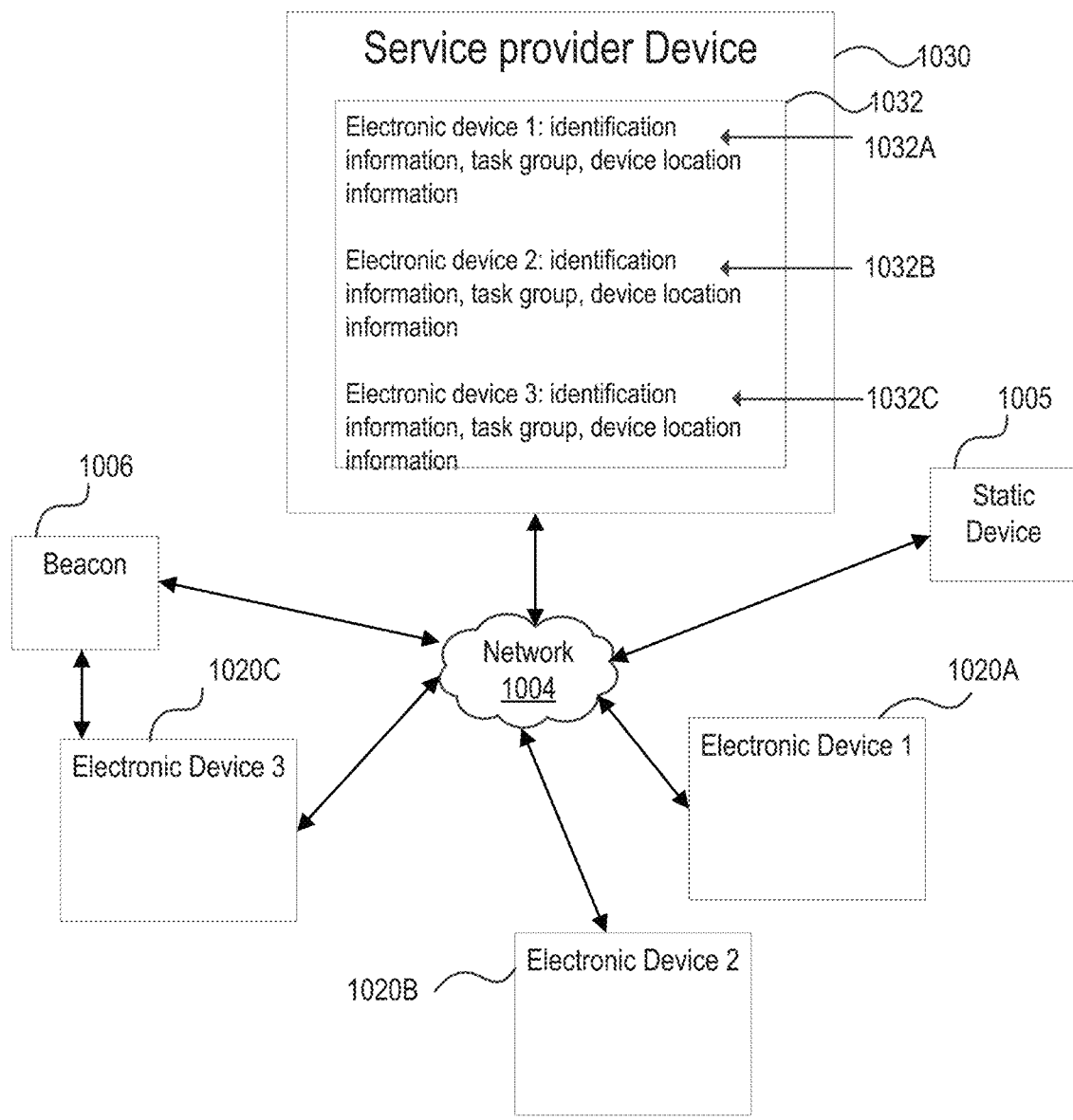
FIG. 10 illustrates a system to selectively forward a communication, consistent with various embodiments.

FIG. 10 illustrates a system to selectively forward a communication, consistent with various embodiments. As shown in FIG. 10, the system may include a service provider device 1030. The service provider device 1030 may include a computing device, such as a computer, server, or series of interconnected servers connected via a network.

The system may include one or more electronic devices 1020A-C. In the embodiment as shown in FIG. 10, three electronic devices are shown (electronic device 1020A-

1020C). However, any number of electronic devices may be included in the system. In some embodiments, an electronic device is a network-accessible device, such as a mobile phone, tablet, computer, etc. In an embodiment, an electronic device is a wearable network-accessible device, such as a smart watch.

As shown in FIG. 10, the service provider device 1030 may access a listing of information relating to each electronic device. In some embodiments, the information relating to each electronic device may be stored in a service provider database 1032. The service provider database 1032 may include information representing data associated with each electronic device. For example, the service provider database 1032 may include data for a first electronic device 1020A and associated identification information, task group information, and device location information, among other information. The service provider database 1032 may include information associated with any number of electronic devices.

For purposes of illustration, the service provider database 1032 includes information relating to a first electronic device 1032A, a second electronic device 10328, and a third electronic device 1032C. Information relating to each electronic device (e.g., 1032A) may be maintained in a subfolder, entry, or a portion of the service provider database 1032.

As shown in FIG. 10, information associated with each electronic device (e.g., 1032A) may include identification information. Identification information may include any information indicative of the identity of the electronic device or an individual associated with the electronic device. Information indicative of an individual (or simply "profile information") may include credentials, a username and password, a code, number, or other information to indicate an identity of an individual. The service provider device 1030 may identify an individual and/or a portion of the database 1032 based on the profile information.

In some embodiments, an electronic device (e.g., first electronic device 1020A) may transmit a message that includes identification information to the service provider device 1030. To identify an individual based on the received identification information, the service provider device 1030 may identify any profile information in the message. For example, the service provider device 1030 may identify credentials in the message. In response to identifying the profile information, the service provider device 1030 may inspect the service provider database 1032 for any entries associated with the profile information. If the service provider device 1030 identifies an appropriate entry (e.g., 1032A), the service provider device 1030 can identify the individual associated with the profile information.

Identification information may include information indicative of an electronic device. Examples of such information may include a device serial number, MAC address, license key, IP address, a specific code, etc. In some embodiments, a message transmitted by an electronic device may include data and/or meta data that indicates electronic device identification information. For example, a message from a first electronic device 1020A may include data representing an IP address of the electronic device. In this example, the service provider device 1030 may inspect the message received for device identification information, such as the IP address of the device.

The service provider device 1030 may inspect the service provider database 1032 to determine whether any received information indicative of an electronic device is associated with a portion of the service provider database 1032. If the service provider database 1032 includes information indicative of an electronic device, the service provider device 1030 may identify associated profile information, task group information, etc. based on the information indicative of an electronic device.

As shown in FIG. 10, the service provider database 1032 may include task group information associated with an individual of the service provider. A task group may include a group of individuals assigned with performing a set of tasks. In some embodiments, each individual is assigned at least one task group, and task group information for each individual is stored in the service provider database 1032. The task group may be assigned to individuals based on experience or skill in a service provider environment. In some embodiments, certain service providers, such as hospitals, may assign task groups based on specialty (e.g., a task group for emergency medical nurses to perform tasks relating to emergency medical procedures). Any individual in a service provider environment may be assigned to one or more task groups based on their role and experience in the service provider environment.

For example, a first task group may include all dentists in a dental practice, where the set of tasks for the first task group include performing dental procedures. This first task group including dentists may be assigned based on the experience of each dentist in the task group, as dentists are generally educated to perform dental procedures. Similarly, a second task group in a dental practice may include support staff members, where the set of tasks for the second task group is administrative tasks, such as data entry and interacting with clients, for example.

As shown in FIG. 10, the service provider device 1030 may include device location information associated with each electronic device. Location information may include information indicative of a location of an electronic device. Location information may include cellular connectivity data (e.g., cell site location information (CSLI)) and/or space satellite connectivity data (e.g., global positioning system (GPS) information). Location information may be utilized in triangulating the geographic position of the electronic device within a network (e.g., a wireless cellular network). In some embodiments, location information may be determined using geotagging data or metadata associated with an Internet Protocol (IP) address of the electronic device.

In some embodiments, the location information of each electronic device stored on the service provider database 1032 may include the most recently received location information. In other words, the service provider device 1030 may periodically receive location information from an electronic device and store such location information in the appropriate portion of the service provider database 1032. The service provider device 1030 may update the location information of the electronic device in the database 1032 upon receipt of the updated location information.

In some embodiments, location information may be based on electronic activity within the service provider environment. Electronic activity may include any event in the service provider environment that is related to profile information and/or device identification information.

An example of electronic activity related to profile information may include logging into a static device 1005, such as a desktop computer, using credentials associated with an individual. Such static devices 1005 may include any network-enabled device with a known location throughout the service provider environment. Examples of static devices 1005 may include desktop computers, wireless access points (WAPs), electronic door locks, sensors, etc. Each static device may include a known location, where the service provider device 1030 may determine the location of the static device based on static device location information stored by the service provider device 1030.

Accordingly, the service provider device 1030 may determine the geographic location of an individual based on profile information received at a static device 1005 in the service provider environment. In an example, if the profile information is used to log into a static device 1005, such as a desktop computer, the service provider device 1030 may determine the geographic location of the individual at the time of the logging into the desktop computer is at or near the static device. The service provider device 1030 may further determine that an individual is within a proximity of the static device 1005 at a specific time if the profile information received by the static device 1005 within a threshold time period before the specific time.

Another example of electronic activity related to device identification information may include the electronic device interacting with one of a plurality of beacons 1006 located throughout the service provider environment. A beacon 1006 may include a network-accessible device configured to communicate with an electronic device and the service provider device 1030 via a network. A beacon may connect to the electronic device using a wireless communication protocol, such as Bluetooth®, near-field communication (NFC), WIFI, etc.

A plurality of beacons (e.g., beacon 1006) may be disposed throughout the service provider environment. Each beacon (e.g., beacon 1006) may include location information stored at the service provider device 1030, where the service provider device 1030 may determine the location of each beacon based on the location information.

In some embodiments, when an electronic device is within a wireless communication range or within a predetermined range of a beacon, the beacon 1006 may connect to the electronic device. As shown in FIG. 10, beacon 1006 may connect to the third electronic device 1020C. When connected, the beacon 1006 may receive identification information indicative of the third electronic device 1020C. The beacon 1006 and the electronic device (e.g., third electronic device 1020C may communicate via a short-range wireless communication protocol, such as Bluetooth®, Near-Field Communication (NFC), etc.

The beacon 1006 may store such identification information and transmit the information and time stamp information indicating the time of the receipt of the information to the service provider device 1030. The service provider device 1030 may receive such information from the beacon 1006 and determine the geographic location of the individual based on the information received from the beacon 1006. The service provider device 1030 may update the service provider database 1032 upon receiving updated location information relating to an individual and an associated electronic device.

Figure 11:
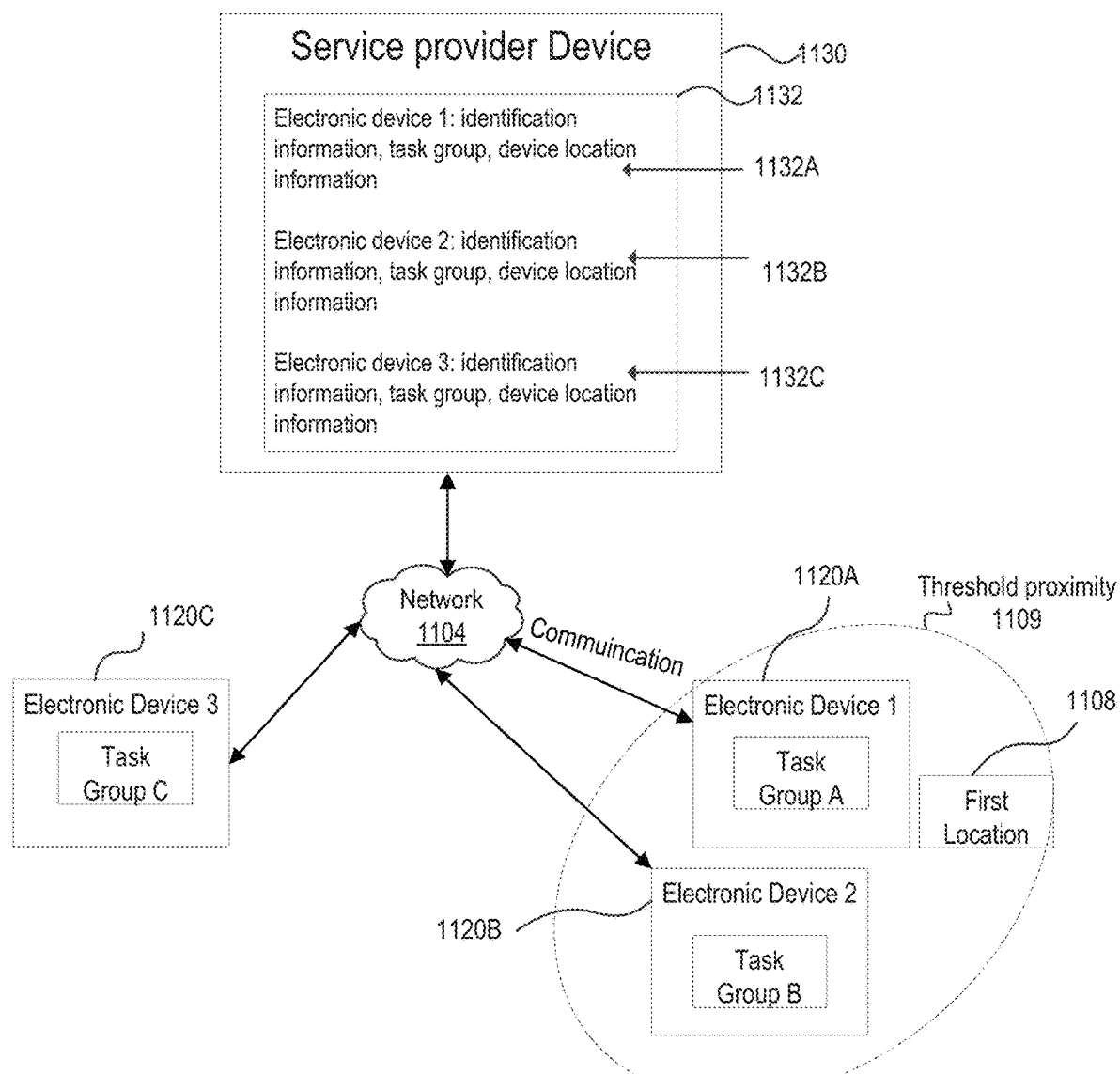
FIG. 11 illustrates a system to selectively forward a communication, consistent with various embodiments.

FIG. 11 illustrates a system to selectively forward a communication, consistent with various embodiments. As shown in FIG. 11, the service provider device 1130 may determine a first location 1108. A first location 1108 may include a desired geographic location within the service provider environment requesting individual(s) to perform a task at the first location 1108. For example, if the communication indicates a request for an individual to interact with a client at a front office, the first location 1108 would include the front office.

The service provider device 1130 may determine the first location 1108 by inspecting a communication for information representing a desired location to perform a task. The service provider device 1130 may utilize feature extraction, character recognition, text recognition, or another similar technique to determine a first location from the communication.

The service provider device 1130 may determine whether each electronic device (e.g., electronic device 1120A-C) is within a threshold proximity 1109 based on the location information stored at the service provider database 1132. A threshold proximity 1109 may include a predetermined distance from the first location identified in the communication. The threshold proximity 1109 may include any distance from the first location, such as 50 feet, 100 feet, 500 feet, etc. Determining the threshold proximity 1009 may include calculating the geographic distance between the geographic location identified in the location information and the first location.

As shown in FIG. 11, some of the electronic devices may be within the threshold proximity 1109. In the embodiment as shown in FIG. 11, for purposes of illustration, the first electronic device 1120A and the second electronic device 1120B may be within the threshold proximity, while the third electronic device 1120C is outside the threshold proximity.

The service provider device 1130 may determine a first task group based on the received communication. The first task group may represent a desired task group to perform a task indicated by the communication. The service provider device 1130 may inspect the communication for task information indicating the task to be performed. The service provider device 1030 may utilize feature extraction, character recognition, text recognition, or another similar technique to determine a first task group from the communication. In some embodiments, the service provider device 1130 may determine a task group based on the task information identified in the communication. For example, the service provider device 1130 may include information relating to each task group, and examples of tasks each task group is capable of performing.

In some embodiments, each individual in the server provider database 1132 is assigned to at least one task group, where each individual includes an associated electronic device. For example, as illustrated in FIG. 11, the first electronic device 1120A is assigned to task group A, the second electronic device 1120B is assigned to task group B, and the third electronic device 1120C is assigned to task group C, where each task group may perform different tasks. In this example, for purposes of illustration, task group A is identified as the first task group identified in the communication, as task group A is equipped to perform the task identified in the communication.

The service provider device 1130 may transmit the communication to all electronic device(s) that are within the threshold proximity of the first location and include a task group associated with the first task group. In the embodiment as shown in FIG. 11, the first electronic device 1120A and the second electronic device 1120B are within the threshold proximity. Accordingly, the third electronic device 1120C is beyond the threshold proximity and may not receive the communication. Additionally, in the embodiment as shown in FIG. 11, the first task group may include task group A. The service provider device 1130 may identify that electronic device 1120A is associated with task group A, and the second electronic device 1120B is associated with task group B. Based on this determination, the service provider device 1130 may determine that the second electronic device 1120B is not equipped to perform the task identified in the communication. Accordingly, the service provider device 1130 may transmit the communication to the first electronic device 1120A, as it is within the threshold proximity and is associated with the first task group.

Figure 12:
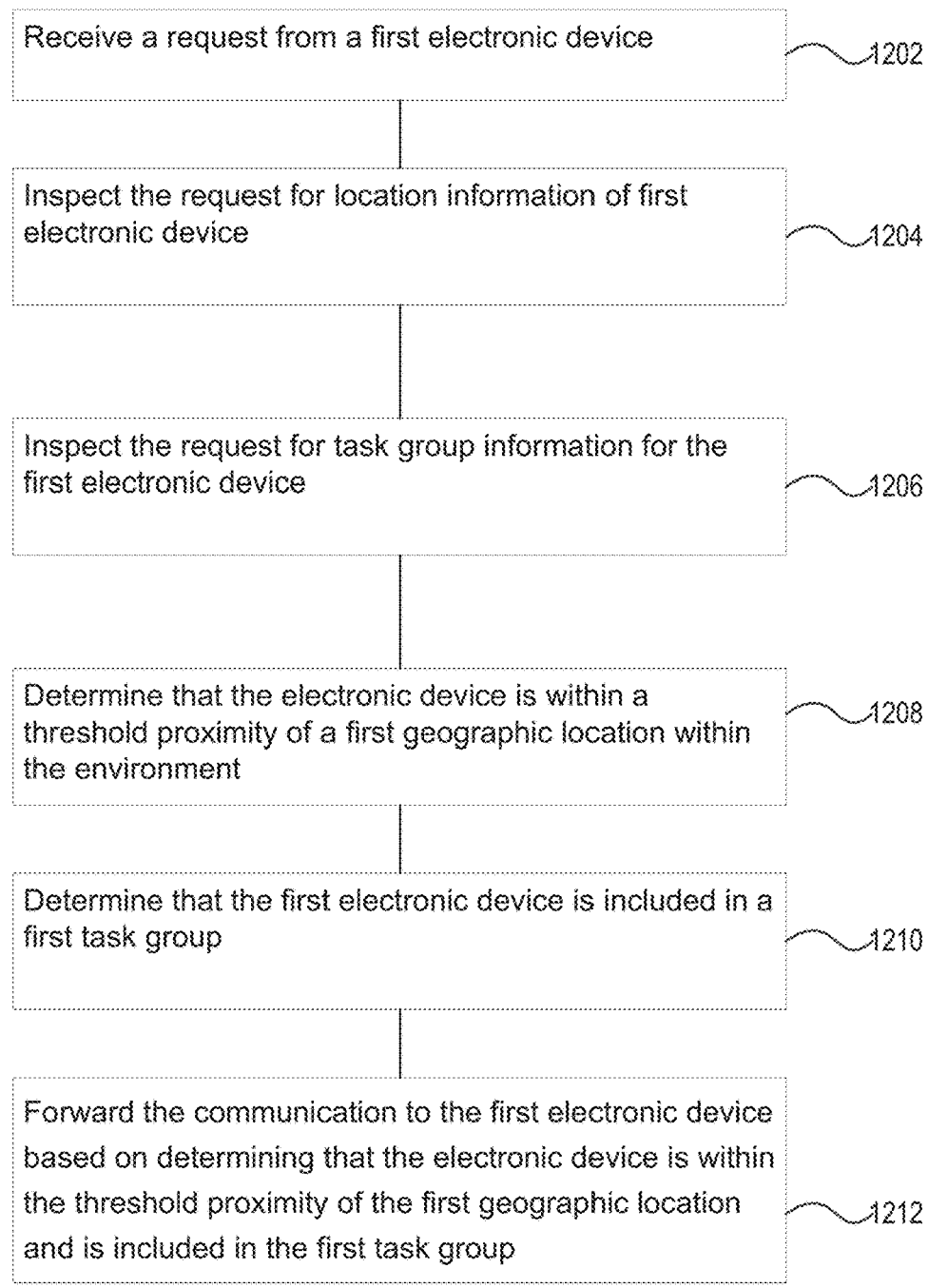
FIG. 12 illustrates a flow diagram illustrating a method to forward a communication, consistent with various embodiments.

FIG. 12 illustrates a flow diagram illustrating a method to forward a communication, consistent with various embodiments. The method includes, at 1202 receiving a request from a first electronic device.

The method includes, at 1204, inspecting the request for location information of first electronic device. The location information may be interpretable by the service provider device to identify a geographic location of the first electronic device.

In some embodiments, the location information includes global positioning system (GPS) data, wherein the service provider device identifies the geographic location of the first electronic device based on inspecting the GPS data.

In some embodiments, the service provider device receives a second request from the first electronic device, where the second request includes updated location information. The service provider device may update the geographic location of the first electronic device based on the updated location information.

In some embodiments, location information of the electronic device is determined by identifying an electronic activity associated with client information indicative of a client.

In some embodiments, the electronic activity associated with the client information includes receipt of credentials associated with client information on a computing device within the environment.

In some embodiments, location information of the first electronic device includes inspecting data from each of a plurality of beacons located within the environment, where each beacon is configured to store client information and timestamp information to identify the geographic location of the first electronic device at a specified time.

The method includes, at 1206, inspecting the request for task group information for the first electronic device. The task group information may be interpretable by the service provider device to identify a task group of the first electronic device.

In some embodiments, the task group of the first electronic device indicates a set of tasks capable of performance by a client associated with the first electronic device.

The method includes, at 1208, determining that the electronic device is within a threshold proximity of a first geographic location within the environment.

The method includes, at 1210, determining that the first electronic device is included in a first task group.

The method includes, at 1212, forwarding the communication to the first electronic device based on determining that the electronic device is within the threshold proximity of the first geographic location and is included in the first task group.

Processing System

Figure 13:
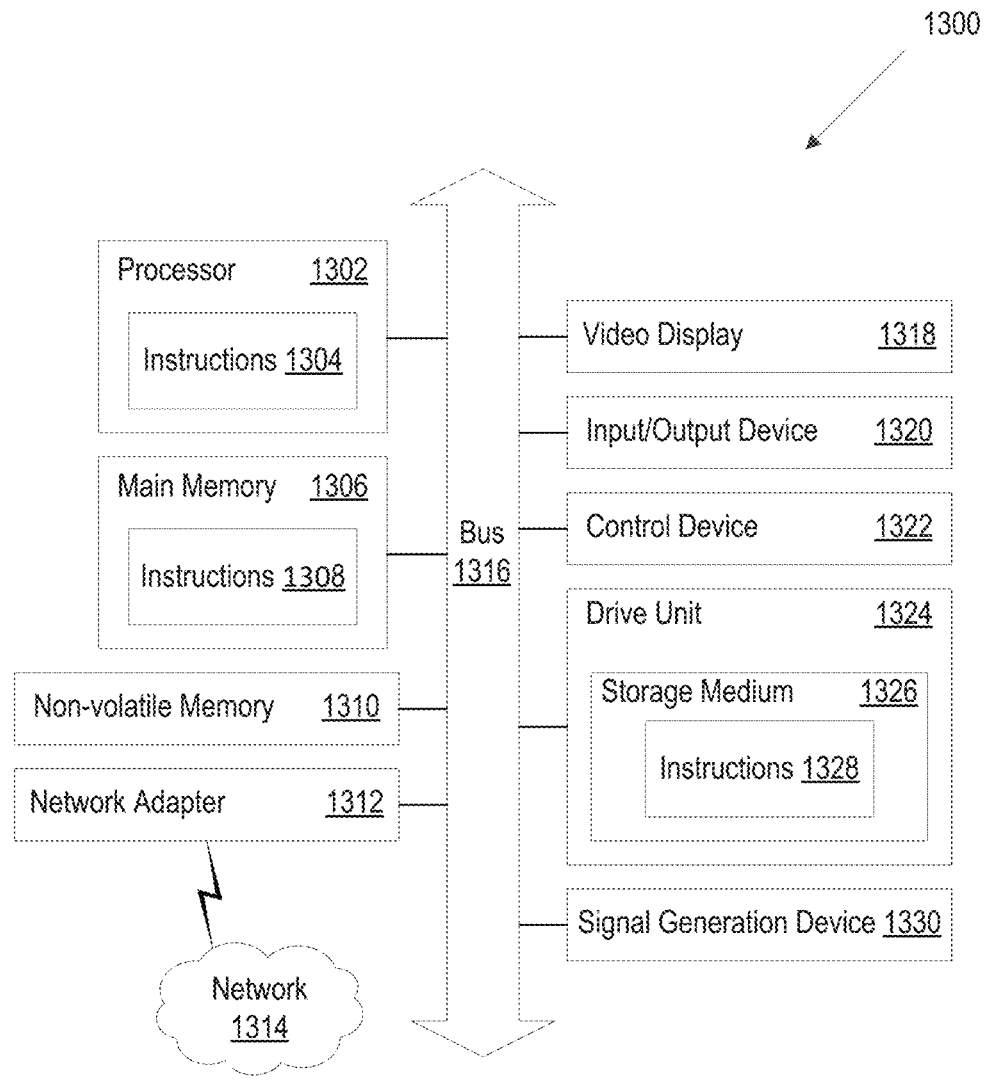
FIG. 13 is a block diagram illustrating an example of a processing system in which at least some operations described herein can be implemented.

FIG. 13 is a block diagram illustrating an example of a processing system 1300 in which at least some operations described herein can be implemented. For example, some components of the processing system 1300 may be hosted on a device (e.g., electronic device 220 of FIG. 2), a service provider device (e.g., service provider device 230 of FIG. 2), or an electronic device on which a mobile application (e.g., computer program 222 of FIG. 2) resides.

The processing system 1300 may include one or more central processing units ("processors") 1302, main memory 1306, non-volatile memory 1010, network adapter 1312 (e.g., network interface), video display 1318, input/output devices 1320, control device 1322 (e.g., keyboard and pointing devices), drive unit 1324 including a storage medium 1326, and signal generation device 1330 that are communicatively connected to a bus 1316. The bus 1316 is illustrated as an abstraction that represents one or more physical buses and/or point-to-point connections that are connected by appropriate bridges, adapters, or controllers. The bus 1316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1300 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1300.

While the main memory 1306, non-volatile memory 1310, and storage medium 1326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1328. The term "machine-readable medium" and "storage medium" shall also be taken to include any medium that is capable of storing, encoding, or carrying a set of instructions for execution by the processing system 1300.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1304, 1308, 1328) set at various times in various memory and storage devices in a computing device. When read and executed by the one or more processors 1302, the instruction(s) cause the processing system 1300 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1310, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1312 enables the processing system 1300 to mediate data in a network 1314 with an entity that is external to the processing system 1300 through any communication protocol supported by the processing system 1300 and the external entity. The network adapter 1312 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1312 may include a firewall that governs and/or manages permission to access/proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

What is claimed is:

1. A method performed by a service provider device to modify a service provider database, the method comprising:
   receiving, by the service provider device, a first communication from a first client device in a first communication format of a plurality of communication formats,
      wherein each communication format is interpretable by the service provider device into a uniform communication format,
      wherein the uniform communication format is a text-based communication format, and
      wherein the first communication includes content that is unknown to the service provider device;
   converting, by the service provider device, the first communication from the first communication format to the uniform communication format,
      wherein the first communication format is an audio communication format, and
      wherein the converting includes transcribing audio from the first communication into text in accordance with the uniform communication format;
   parsing, by the service provider device, the text of the first communication in the uniform communication format based on feature extraction, character recognition, or text recognition;
   discovering, by the service provider device, based on the parsed text of the first communication, a request to modify an electronic schedule of a plurality of events stored in the service provider database,
      wherein the electronic schedule is maintained in the uniform communication format, and
      wherein the electronic schedule is associated with a plurality of clients including the first client device;
   selecting, by the service provider device, a modification rule of a plurality of modification rules based on a similarity analysis between the parsed text of the first communication and a keyword of the modification rule,
      wherein each modification rule is generated in accordance with a machine learning technique based on a discovery of connections between terms of the electronic schedule and modifications to the electronic schedule based on associations between previous requests to modify the electronic schedule and one or more of the plurality of modification rules;
   modifying, by the service provider device, the electronic schedule in accordance with the request based on evaluating the request according to the selected modification rule of the plurality of modification rules; and
   sending, by the service provider device, a second communication in a second communication format of the plurality of communication formats,
      wherein the second communication format is selected based on an association between the first client device and the service provider database, and
      wherein the second communication indicates that the electronic schedule has been modified in accordance with the request or seeks information required to complete the modification of the electronic schedule.

2. The method of claim 1, wherein the service provider database includes a medical records database that includes one or more medical records entries associated with the plurality of clients and a personal information database that includes personal information entries associated with the plurality of clients.

3. The method of claim 1, further comprising:
   receiving a third communication from the first client, where the third communication indicates a selected event in the schedule; and
   modifying the selected event in the schedule indicated by the third communication to include information identifying the first client.

4. The method of claim 1, wherein parsing the first communication further comprises inspecting the request for information identifying the first client.

5. The method of claim 4, wherein information identifying the first client includes a mobile phone number associated with a mobile phone of the first client.

6. The method of claim 5, wherein the information identifying the first client includes a mobile phone number associated with a mobile phone of the first client.

7. The method of claim 1, further comprising:
   receiving a fourth communication from a second client;
   identifying a communication format of the fourth communication;
   determining whether the communication format of the fourth communication matches the communication format of the first communication; and
   converting the second communication format to the first communication format based on determining the second communication format does not match the first communication format.

8. The method of claim 1, wherein the first client device includes a mobile phone, wherein the mobile phone includes instructions to execute a mobile application.

9. The method of claim 1, further comprising:
   inspecting the schedule for an available event that has a time duration greater than or equal to an estimated time duration of an event associated with the client; and
   updating the available event to include information associating the available event to the first client and remove any client identification information from the event associated with the first client.

10. The method of claim 2, further comprising:
    transmitting a medical record entry within the medical record database to a third-party device, wherein the medical record entry is encrypted, and wherein the third-party device is configured to decrypt the medical record entry.

11. A service provider device, comprising:
a processor; and
a memory storing instructions that, when executed by the processor,
cause the processor of the service provider device to:
convert a first communication received from a first client device from a first communication format of a plurality of communication formats to a uniform communication format,
    wherein the first communication format is an audio communication format,
    wherein the uniform communication format is a text-based communication format,
    wherein the first communication includes content is unknown to the service provider device, and
    wherein audio from the first communication is transcribed into text in accordance with the uniform communication format;
parse the text of the first communication in the second communication format based on feature extraction, character recognition, or text recognition,
discover, based on the parsed text of the first communication, a request to modify an electronic schedule of a plurality of events stored in a service provider database,
    wherein the electronic schedule is maintained in the uniform communication format, and
    wherein the schedule is associated with a plurality of clients including the first client device;
select a modification rule of a plurality of modification rules based on a similarity analysis between parsed text of the first communication and a keyword of the modification rule,
    wherein each modification rule is generated in accordance with a machine learning technique based on a discovery of connections between terms of the electronic schedule and modifications to the electronic schedule based on associations between previous requests to modify the electronic schedule and one or more of the plurality of modification rules;
modify the electronic schedule in accordance with the request based on evaluating the request according to the selected modifications rule of the plurality of modification rules; and
transmit a second communication in a second communication format of the plurality of communication formats,
    wherein the second communication format is selected based on an association between the first client device and the service provider database, and
    wherein the second communication indicates that the electronic schedule has been modified in accordance with the request or seeks information required to complete the modification.

12. The service provider device of claim 11, wherein the second communication in one of the plurality of communication formats selected to the first client includes the first communication format.

13. A service provider device, comprising:
a processor; and
a memory storing instructions that, when executed by the processor,
cause the processor of the service provider device to:
convert a first communication received from a first client device from a first communication format of a plurality of communication formats to a uniform communication format,
    wherein the first communication format is an audio communication format,
    wherein the uniform communication format is a text-based communication format,
    wherein the first communication includes content that is unknown to the service provider device, and
    wherein audio from the first communication is transcribed into text in accordance with the uniform communication format;
parse the text of the first communication in the second communication format based on feature extraction, character recognition, or text recognition,
discover, based on the parsed text of the first communication, a request to modify an electronic schedule of a plurality of events stored in a service provider database,
    wherein the electronic schedule is maintained in the uniform communication format, and
    wherein the schedule is associated with a plurality of clients including the first client device;
select a modification rule of a plurality of modification rules based on a similarity analysis between parsed text of the first communication and a keyword of the modification rule,
    wherein each modification rule is generated in accordance with a machine learning technique based on a discovery of connections between terms of the electronic schedule and modifications to the electronic schedule based on associations between previous requests to modify the electronic schedule and one or more of the plurality of modification rules;
modify the electronic schedule in accordance with the request based on evaluating the request according to the selected modification rule of the plurality of modification rules; and
transmit a second communication in a second communication format of the plurality of communication formats,
    wherein the second communication format is selected based on an association between the first client device and the service provider database, and
    wherein the second communication indicates that the electronic schedule has been modified in accordance with the request or seeks information required to complete the modification.

14. The method of claim 13, further comprising:
transmitting a third communication to the potential client indicating that the event has been modified to include information identifying the potential client.

15. The method of claim 13, wherein the service provider device maintains the service provider database and a listing of potential events in a potential event registry.

16. The method of claim 1, wherein the service provider database includes a plurality of procedure codes, wherein each procedure code is associated with a procedure to be performed by a service provider.

17. A method performed by a service provider device to modify a service provider database, the method comprising:
- converting, by the service provider device, a first communication from a first client from a first communication format to a uniform communication format,
  - wherein the first communication format is an audio communication format,
  - wherein the uniform communication format is a text-based communication format,
  - wherein the first communication includes content that is unknown to the service provider device, and
  - wherein the converting includes transcribing audio from the first communication into text in accordance with the uniform communication format;
- parsing, by the service provider device, the text of the first communication in the uniform communication format based on feature extraction, character recognition, or text recognition;
- discovering, by the service provider device, based on the parsed text of the first communication, a request to modify an event associated with the first client device,
  - wherein the event is part of an electronic schedule of a plurality of events stored in the service provider database,
    - wherein the electronic schedule is associated with a plurality of clients including the first client;
- selecting, by the service provider device, a modification rule of a plurality of modification rules based on a similarity analysis between the parsed text of the first communication and a keyword of the modification rule,
  - wherein each modification rule is generated in accordance with a machine learning technique based on a discovery of connections between terms of the electronic schedule and modifications to the electronic schedule based on associations between previous requests to modify the electronic schedule and one or more of the plurality of modification rules;
- removing, by the service provider device, information identifying the first client from the event associated with the first client based on evaluating the request according to the selected modification rule of the plurality of modification;
- identifying, by the service provider device, a potential client different than the first client in a listing of potential clients, wherein the potential client accepts a proposed scheduling to update the event to include the information identifying the potential client in a second communication; and
- upon receiving the second communication from the potential client indicating an acceptance of proposed scheduling, modifying, by the service provider device, the event to include the information identifying the potential client.

18. The method of claim 17, further comprising:
transmitting a third communication to the potential client indicating that the event has been modified to include the information identifying the potential client.

19. The method of claim 1, further comprising:
receiving, location information from the first client device; and
updating the service provider database to include the location information.

20. The method of claim 1, further comprising:
identifying, based on the parsed text of the first communication, a client profile associated with an event of the plurality of events,
- wherein modifying the electronic schedule in accordance with the request includes modifying the event of the plurality of events.

* * * * *